United States Patent
Kurtz et al.

(10) Patent No.: US 6,301,330 B1
(45) Date of Patent: Oct. 9, 2001

(54) APPARATUS AND METHOD FOR TEXTURE ANALYSIS ON SEMICONDUCTOR WAFERS

(75) Inventors: David S. Kurtz; Krzysztof J. Kozaczek, both of State College; Paul R. Moran, Port Matilda, all of PA (US)

(73) Assignee: HyperNex, Inc., State College, PA (US)

( * ) Notice: Subject to any disclaimer, the term of this patent is extended or adjusted under 35 U.S.C. 154(b) by 0 days.

(21) Appl. No.: 09/365,063

(22) Filed: Jul. 30, 1999

(51) Int. Cl.$^7$ ............... G01N 23/223; G01N 23/20; G01N 23/207
(52) U.S. Cl. ............... 378/71; 378/70; 378/73; 378/79; 378/44; 378/45
(58) Field of Search ............... 378/70, 73, 79, 378/71, 44, 45

(56) References Cited

U.S. PATENT DOCUMENTS 6,005,914 * 12/1999 Quinn et al. ............... 378/81
6,064,717 * 5/2000 Ortega et al. ............... 378/71

FOREIGN PATENT DOCUMENTS

2910534 * 9/1980 (DE) .

OTHER PUBLICATIONS

Bunge et al, Determination of Quantitative, High–resolution Pole Figures with the Area Detector, Z. Metallkd.87 (1996) 6, p. 465–475.*
S. Matthies et al., "On the reproduction of the orientation distribution function of texturized samples from reduced pole figures using conception of a conditional ghost correction," Phys. Stat. Sol. (b) 112 (1982) K111–K114.
K. Pawlik, "Determination of the Orientation Distribution Function from Pole Figures in Arbitrarily Defined Cells" Phys. Stat. Sol. (b) 124 (1986), 477.
S. Matthies, On the reproducibility of the orientation distribution function of texture samples from pole figures (ghost phenomena), Phys. Stat. Sol. (b) 92 (1979), K135–K138.
Bruker 1997 Catalog, Order No. B88–E00001.
H.J. Bunge, H Klein, "Determination of Quantitative, High Resolution Pole Figures with the Area Detector", Z. Metallkd., 87 (6) P 465–475, (1996).
K.L. Smith and R.B. Ortega, "Use of a Two–dimensional Position Sensitive Detector for Collecting Pole Figures," Advances in X–ray Analysis, 36 (1993) 641–647.

* cited by examiner

Primary Examiner—Frank G. Font
Assistant Examiner—Armando Rodriguez
(74) Attorney, Agent, or Firm—Steven J. Hultquist; Marianne Fuierer

(57) ABSTRACT

An apparatus and method for performing rapid, high-resolution polycrystalline crystallographic texture analysis, by calculating an Orientation Distribution Function (ODF) from partial pole figures obtained from x-ray diffraction measurements on large samples, e.g., 200 millimeter diameter wafers. The measurement apparatus includes a 2-D area x-ray detector and a collimated x-ray source arranged in a specific, fixed spatial relationship dependant on the properties of the sample to be measured, and also includes a particular wafer motion assembly. The wafer motion assembly includes three mutually orthogonal rectilinear translation stages, and a $\phi$ rotation stage mounted thereon, as an uppermost motion stage, with its range restricted to 180° of rotation. $\theta$–2$\theta$ and $\chi$ motions are eliminated, and the close deployment of the x-ray source and area detector to the measuring spot on the wafer is such that the detector covers a sufficient range of 2$\theta$ and $\chi$ to capture multiple diffraction arcs in each frame. The invention employs a new and advantageous texture analysis protocol to determine ODF from the severely truncated pole figures thus obtained, through comparison of experimental ODF figures with calculated ones. The resulting system is fast, accurate, amenable to automation, and does not require highly skilled personnel to operate.

40 Claims, 13 Drawing Sheets

PREFERRED POSITION OF AREA X-RAY DETECTOR

HIT REPORT ABOUT ALL IZPOL POLE FIGURE

| | | |
|---|---|---|
| MINIMUM = 3 | BET = 65 | GAM = 60 |
| MAXIMUM = 0 | BET = 96 | GAM = 85 |

```
BET>9089800786858483828180797877767574737271706968676665646362616059585755655
GAM
451    4 4 4 4 4 4 4 4 4 4 4 4 4 4 4 4 5 5 6 6 6 6 6 6 6 6 6 6 6 6 6 6 6 6 5 5 5 5 5 4 4 · · · · ·
461    4 4 4 4 4 4 4 4 4 4 4 4 4 4 4 4 5 5 6 6 6 6 6 6 6 6 6 6 6 6 6 6 6 6 5 5 5 5 5 4 4 · · · · ·
471    4 4 4 4 4 4 4 4 4 4 4 4 4 4 4 4 5 5 6 6 6 6 6 6 6 6 6 6 6 6 6 6 6 6 5 5 5 5 5 4 4 · · · · ·
481    4 4 4 4 4 4 4 4 4 4 4 4 4 4 4 4 5 5 5 6 6 6 6 6 6 6 6 6 6 6 6 6 6 5 5 5 5 5 4 4 · · · · · ·
491    4 4 4 4 4 4 4 4 4 4 4 4 4 4 4 5 5 5 5 6 6 6 6 6 6 6 6 6 6 6 6 6 5 5 5 5 5 4 4 · · · · · · ·
501    4 4 4 4 4 4 4 4 4 4 4 4 4 4 5 5 5 5 5 6 6 6 6 6 6 6 6 6 6 6 6 5 5 5 5 4 4 · · · · · · · · ·
511    4 4 4 4 4 4 4 4 4 4 4 4 4 5 5 5 5 5 5 6 6 6 6 6 6 6 6 6 6 6 5 5 5 5 4 4 · · · · · · · · · ·
521    4 4 4 4 4 4 4 4 4 4 4 4 5 5 5 5 5 5 5 5 6 6 6 6 6 6 6 6 6 5 5 5 5 4 4 · · · · · · · · · · ·
531    4 4 4 4 4 4 4 4 4 4 4 5 5 5 5 5 5 5 5 5 6 6 6 6 6 6 6 6 5 5 5 5 4 4 · · · · · · · · · · · ·
541    4 4 4 4 4 4 4 4 4 4 5 5 5 5 5 5 5 5 5 5 6 6 6 6 6 6 6 5 5 5 5 4 4 · · · · · · · · · · · · ·
551    4 4 4 4 4 4 4 4 4 5 5 5 5 5 5 5 5 5 5 5 6 6 6 6 6 6 5 5 5 5 4 4 · · · · · · · · · · · · · ·
561    4 4 4 4 4 4 4 5 5 5 5 5 5 5 5 5 5 5 5 5 6 6 6 6 6 5 5 5 5 4 4 · · · · · · · · · · · · · · ·
571    4 4 4 4 4 5 5 5 5 5 5 5 5 5 5 5 5 5 5 5 6 6 6 6 5 5 5 5 5 5 6 7 · · · · · · · · · · · · · · ·
581    4 4 4 4 5 5 5 5 5 5 5 5 5 5 5 5 5 5 5 5 6 6 5 5 5 5 5 6 6 7 · · · · · · · · · · · · · · · · ·
591    4 4 5 5 5 5 5 5 5 5 5 5 5 5 5 5 5 5 5 5 5 5 5 5 5 5 6 7 · · · · · · · · · · · · · · · · · · ·
601    4 5 5 5 5 5 5 5 5 5 5 5 5 5 5 5 5 5 5 5 5 5 5 5 5 6 7 · · · · · · · · · · · · · · · · · · · ·
611    4 5 5 5 5 5 5 5 5 5 5 5 5 5 5 5 5 5 5 5 5 5 4 3 4 · · · · · · · · · · · · · · · · · · · · · ·
621    4 5 5 5 5 5 5 5 5 5 5 4 4 4 4 4 · · · · · · · · · · · · · · · · · · · · · · · · · · · · · · ·
631    3 4 4 4 4 4 4 4 4 4 4 · · · · · · · · · · · · · · · · · · · · · · · · · · · · · · · · · · · ·
```

APPARATUS AND METHOD FOR TEXTURE ANALYSIS ON SEMICONDUCTOR WAFERS

BACKGROUND OF THE INVENTION

1. Field of the Invention

The present invention generally relates to the field of semiconductor manufacturing, and more specifically to crystallographic texture measurement and analysis systems for polycrystalline materials on wafers.

2. Background of the Invention

The physical properties of single crystals, such as electric, elastic, and magnetic properties, are directionally dependent and usually represented by tensors of the second, fourth and sixth order, respectively. As a consequence, a polycrystalline material, which is an aggregate of single crystals (called grains or crystallites), has anisotropic properties. The degree of anisotropy of a macroscopic specimen depends on the orientation distribution of its crystallites, or texture, with respect to the sample fixed coordinate system.

As an example, most thin film metallization processes for semiconductor applications result in a preferred orientation of grains with respect to growth surface. The crystallographic texture of thin films and discrete structures used in integrated circuits greatly affects their reliability and performance, and may be controlled by tunable manufacturing processes. A discussion of the importance of texture and disclosure of texture control methods is found in the paper titled "Microstructure Control in Semiconductor Metallization", J. M. E. Harper, K. P. Rodbell, J. Vac. Sci. Technology, 15 (4), 763–779, (1997).

The quantitative measure of texture can be described by the so-called Orientation Distribution Function (ODF) which permits one to describe texture in a rigorous mathematical way and to calculate the macroscopic properties from the corresponding single crystal properties. However, a direct method of ODF measurement has not been developed. The experimental determination of ODF is currently only performed by destructive and time-consuming measurements of orientation and volume of large numbers of individual grains, subsequent mathematical analysis of which then yields a unique ODF for the sample of interest.

X-ray diffraction is a well-known technique for measuring the physical properties of polycrystalline materials. See, for example, H. P. Klug, L. E. Alexander, "X-ray Diffraction Procedures", Wiley & Sons, (1974). X-rays diffracted from the surface of a polycrystalline material provide direct information about the size, spacing, and orientation of crystallites that comprise the polycrystalline material. X-rays impinging on the material will scatter in all directions. Constructive interference of the scattering x-rays occurs only at particular angles that the scattering x-rays make with the incident x-ray beam, and is dependent on the crystalline spacing and orientation. This information is represented in the form of diffracted x-ray intensity versus the diffraction angle from incident beam. Constructive interference of scattered x-rays from the crystalline structure results in intensity maxima, also referred to as diffraction peaks. Each particular set of crystalline structures of a material will have an associated diffraction peak that occurs at a particular angle.

There exist numerous commercial x-ray diffraction instruments that measure the physical properties from which the texture of polycrystalline materials may be determined, including those produced by Philips Analytical X-ray, Bruker AXS, Rigaku International Corp., Scintag Inc., Bede Scientific Inc. and others. However, use of these systems for texture determination, while feasible, is nonetheless time-consuming, lacks sufficient resolution, and is limited to relatively small semiconductor wafers. Furthermore, these current systems contain inherent limitations that make their conversion to a rapid, high precision measurement tool for large uncut wafers (e.g., 200 millimeter diameter, and recently introduced 300 millimeter diameter) problematic. The speed of measurement, obtainable measurement resolution, and applicable wafer size remain as limitations of the state of the art in texture analysis of semiconductor wafers.

Using an area x-ray detector on an x-ray diffraction instrument increases the speed of texture analysis considerably, but area x-ray detectors are not currently used as efficiently as possible for texture analysis. This is primarily due to the fact that they employ traditional texture analysis protocols that do not efficiently use all of the diffraction information captured by the area detector. The resultant measurement time is still quite long. As a consequence, fewer samples are typically analyzed due to the excessive measurement times required.

Motion control systems have been built into x-ray diffraction systems for the mapping of texture over the surface of a large (e.g., 150 millimeter) wafer, but they too are not designed to make the most efficient use of diffraction information obtained from the area detector. Such motion control systems also tend to be complex and very expensive. Even if current x-ray diffraction systems utilizing area detectors were converted to map texture in larger wafers (by increasing the size of the texture mapping stages), they would be extremely inefficient, complex, costly, and slow. Efficient integration of a wafer motion system (for mapping texture over the entire wafer surface) with an area x-ray detector has not been achieved with the currently available instruments.

The current texture analysis methodologies additionally are not suitable for new generations of materials (such as polycrystalline and epitaxial films, or superconductors) that have sharp textures. The methods lack the required resolution, do not take advantage of the sample and crystal symmetry in order to expedite testing, and do not take advantage of modern computing capabilities. The current texture analysis methodologies do not make efficient use of all the diffraction data captured on an area x-ray detector. While texture analysis using current commercial x-ray systems is versatile, it is tedious, slow and requires a highly trained operator. The present systems are not practical for large sample throughput rates and automated operation, as would be required for commercial manufacturing operations.

Considering texture analysis and the state of the art in more specific detail, the Orientation Distribution Function (ODF), the quantitative measure of texture, can be described in G-space, where the orientation g of an individual crystallite with respect to the reference system of the sample is described by three independent parameters (usually angles) $g=\{\alpha, \beta, \gamma\}$. A schematic representation of G-space is shown in FIG. 1. A direct method of ODF measurement does not exist. The experimental determination of ODF, as mentioned hereinabove, is possible through destructive and time consuming measurements of orientation and volume of large numbers of individual grains, which yield a unique ODF (see K. Lucke, H. Perlwitz, and W. Pitsch, "Elekronenmikroskopische Bestimmung der Orientierungsferteilung der Kristallite in gevaltztem Kupfer," Phys. Stat. Sol. 7 (1964), 733–746, and F. Wagner "Texture Determination by Individual Orientation Measurement," in Experimental Techniques in Texture Analysis, ed. H. J. Bunge (DGM, Oberusel, 1986), 115–124).

The more practical and nondestructive experimental method is the direct measurement of a volume of crystallites with two of the three angular parameters fixed and the third parameter varied through all possible values. This is the so-called pole figure measurement. The ODF is subsequently calculated from several pole figures (pole figure inversion). The term "pole figure" is understood as the intensity distribution of a certain physical quantity in reference to the sample coordinate system. The pole figure measurement is most commonly obtained by diffraction (of x-rays, neutrons or electrons). The measured physical quantity in this case is the intensity of x-rays diffracted from a particular set of crystallographic planes. The central problem of quantitative texture analysis is the reproduction of the ODF from experimental pole figures. The original works of Bunge (H. J. Bunge, Texture Analysis in Materials Science (Butterworths, London, 1982)), Roe (R. J. Roe, "Description of crystalline orientation in polycrystalline materials. (III) General solution to pole figure inversion," J. Appl. Phys. 36 (1965), 2024– 2031) and Matthies (S. Matthies, "On the reproducibility of the orientation distribution function of texture samples from pole figures (ghost phenomena), Phys. Stat. Sol. (b) 92 (1979), K135–K138) have been followed by newer methods (K. Pawlik, Phys. Stat. Sol. (b) 124 (1986), 477).

The experimental methods of pole figure measurement are classified into two groups: 1) a constant diffraction vector method and 2) a variable diffraction vector method. In the constant diffraction vector method, the sample is rotated in such a way that each sample direction is brought successively into the direction of the diffraction vector, as shown in FIG. 2. This requires at least two independent sample rotations. Usually, the fixed diffraction vector method of pole figure measurement is performed on a four axis goniometer that allows for three independent sample rotations $\omega$, $\phi$, and $\chi$, and one detector rotation $2\theta$ as shown in FIG. 3. The three rotations can be combined in many different ways in order to scan all the sample directions. The most common methodology is to fix $\omega$ and rotate $\phi$ in the range 0–360° and $\chi$ in the range 0–90°. In practice the maximum $\chi$ is reduced to 75–85° due to high defocusing errors at higher tilt angles. Reducing the $\chi$ rotation to less than 90° results in a so-called incomplete pole figure. A complete pole figure may be constructed by combining the transmission and reflection measurements as recommended in American Society for Testing and Materials Standard E81-96, "Standard Test Method for Preparing Quantitative Pole Figures". Such a method required that a very thin isolated foil of material being tested be prepared and therefor is not practical as part of a commercial test method. Only one crystallographic reflection is used at a time in the fixed diffraction vector method. In this case the point detector is fixed at a given $2\theta$ corresponding to a particular crystallographic plane.

In the variable diffraction vector method, the incident and diffracted beams are rotated with respect to a sample. The sample is rotated only through one angle. Such an arrangement is commonly used in electron diffraction in electron microscopes. Both aforementioned methods of pole figure measurement measure only one pole figure at a time.

Even though the pole figures are continuous functions, their measurement is carried out in a sequence of discrete steps. One major drawback of the apparatus and measurement protocol described above is that it is relatively slow due to the large number of sequential scanning steps required with a point detector. Usually the pole figures are scanned in 5° steps in $\phi$ and $\chi$ in order to keep the total measurement time at a reasonable level. Even so, measurements can require up to several hours. For example, there would be 72 $\phi$ positions (0° to 360° in 5° steps) and 17 $\chi$ positions (0° to 85° in 5° steps) for a total of 1224 measurement points in a single pole figure. Assuming a typical collection time of 10 seconds per position, the total data collection time would be 3.4 hours per pole figure. For the ODF calculation for a cubic material one usually needs three pole figures, which would result in 10.2 hours for data collection. This total collection time does not account for the necessary corrections of the raw experimental data, and the computing time to calculate the ODF, which traditionally has also been a long procedure due to limitations on available computing power. Thus, the excessive measurement times required to obtain pole figures independently using a point detector represent a significant shortcoming of the prior art. A further significant disadvantage resulting from the long measurement times required by this approach is that the 5° step scan can miss significant information in highly textured materials. In such materials texture can change quite dramatically within a range of 10°. Thus, higher resolution measurements and analysis are required.

The conventional method of pole figure measurement uses a scanning point detector fixed at $2\theta$ position and which registers the integral intensity of diffracted energy (optical, x-ray, neutron, electron, etc.). In the last decade, position sensitive detectors have seen some limited application to texture analysis (L. Wcislak, H. J. Bunge, Texture Analysis with a Position Sensitive Detector, (Cuvillier, Gottingen, 1996)). More recently two dimensional (2-D) area x-ray detectors (also referred to as position sensitive detectors or PSDs) have been used to measure texture much faster than traditional point detectors by measuring a range of angular directions simultaneously {[H. J. Bunge, H. Klein, "Determination of Qunatitative, High Resolution Pole Figures with the Area Detector", Z. Metallkd., 87 (6), P 465–475, (1996)], [K. L. Smith and R. B. Ortega, "Use of a Two-dimensional Position Sensitive Detector for Collecting Pole Figures," Advances in X-Ray Analysis, 36 (1993) 641–647], [U. Preckwinkel, K. Smith, B. He, B. Schey, B. Stritzker, "Texture Analysis in Thin Films Using an Area Detector", Presented at 47th Annual Denver X-ray Conference Aug. 3–7, Colorado Springs, Colo., (1998)]}. The active face of the 2-D area detector can be thought of as a tightly packed planar array of micro-detectors, all of which operate simultaneously. U.S. Pat. No. 5,828,784 issued to Kurtz, discloses a representative area detector.

Rather than forcing a sequential scan of the sample in two angular directions ($\chi$ and $\phi$) to create an intensity "map" as required by point detectors, the area detector allows concurrent measurement over a large range of one direction, namely the $\chi$ direction, while located at one position, as shown in FIG. 4. The range of $\phi$ covered by the area detector is much less. The ranges of $\chi$ and $\phi$ depend on the measurement geometry, and in particular on the detector to measurement point distance. However, the area detector can typically observe more than one diffraction peak (crystallographic reflection) at a time. FIG. 4 shows the diffraction arcs corresponding to three crystallographic planes, captured on a single collection frame of the area x-ray detector. Thus the area detector can provide a range of $\chi$ and $\phi$ values (though the range in $\chi$ is much greater than the range in $\phi$) for several crystallographic planes in one collection frame, which is equivalent to collecting several incomplete pole figures simultaneously. This results in much shorter data collection time compared to a point detector, that must sequentially scan an equivalent angular range.

Another primary advantage of using an area position sensitive detector is the registration of complete peak profiles and background profiles, instead of just integral intensities at only one point, as from a point detector. Thus the intensity can be integrated over the entire peak width and the background scattering can be subtracted out. This results in greatly improved intensity counting statistics and reduction of the measuring error.

By way of illustrative example and not limitation, one type of area x-ray detector suitable for texture analysis in polycrystalline materials is a multiwire gas proportional counter, e.g., the device manufactured by Bruker AXS (Madison, Wis., 608-276-3047) and commercially available under the product name HI-STAR. Bruker also produces a complete x-ray diffraction system based on the HI-STAR detector. It is sold under the product name GADDS (General Area Detector Diffraction System). The HI-STAR detector features extremely high sensitivity combined with a total detection area 11.5 centimeters in diameter. Compared to other types of x-ray detectors, the multiwire gas detector has slightly poorer angular resolution (presently around 150 $\mu$m), but for texture analysis, particularly on thin polycrystalline films, sensitivity is generally more important than angular resolution. The large 2-D area of the HI-STAR detector allows for the simultaneous collection of diffraction intensity over a large range of $\chi$ angles and $2\theta$ angles. The x-ray diffraction data shown in FIG. 4 was collected on thin copper film using a HI-STAR detector.

The exact range of $2\theta$, $\chi$ and $\phi$ covered by the area detector depends on its distance from the sample. As the area detector is moved closer to the irradiated spot on the sample, the angular range of $2\theta$, $\chi$, and $\phi$ covered by the area detector increases. As the area detector is moved farther away from the irradiated spot on the sample, the angular range of $2$, $\chi$, and $\phi$ covered by the area detector decreases.

The present texture analysis protocols and software for the commercial GADDS x-ray diffraction system accommodate analysis of only one reflection (diffraction arc) at a time like a traditional diffractometer, essentially forcing the user to go back and reconfigure the system to analyze texture on a second or third reflection in separate steps. Thus, even though the detector might be collecting information on several diffraction peaks in any one frame, the data are not analyzed simultaneously.

The ODF reproduction from pole figures can only be solved numerically in practice (as opposed to a analytical mathematical solution). The analysis, historically developed for structural and geological materials, has been optimized for 5° steps in experimental pole figures. The primary reasons for the 5° steps were a practical limitation in data collection times and limitations on computing power.

The commercially available software supplied with texture goniometers (Bruker AXS, Phillips, Rigaku, Scintag, Seifert) or as a software package only (PopLA {Preferred Orientation Package-Los Alamos, U. F. Kocks, J. S. Kallend, H. R. Wenk, A. D. Rollet, and S. I. Wright, Los Alamos National Laboratory}, Beartex {The Berkeley Texture Package, University of California at Berkeley}, LaboTex {Labosoft, Krakow, Poland} use pole figures measured with a 5° resolution for the ODF analysis. The computation time is several minutes since the algorithms do not make use of modem computing capabilities and are not optimized for speed. Decreasing the step to 1° would increase the computation time by a factor of 125, making it impractical for many of today's highly textured engineering/electronic materials. Examples of such materials are semiconductor thin films, particularly metallization layers, which often have very sharp textures. The ODF analysis for such materials requires a higher resolving power while collecting pole figures. For the metallization blanket films and interconnects, the required resolution is 1 degree or less. However, a suitably fast measurement will always be preferred for a practical commercial instrument. The methodology of calculating the ODF from high resolution pole figure data collected with variable resolution has not been developed nor published to date.

Most traditional x-ray texture goniometers are not capable of handling large size samples, or mapping over the surfaces of large samples. Recently some manufacturers of commercial x-ray diffractometers such as Bruker, Philips, Scintag, Seifert, and Rigaku have offered mapping stages (x, y, z translations, and $\phi$ rotation) that are built onto an Eulerian cradle. These stages are primarily designed for thin wafers, as used in the electronics industry. The Eulerian cradle is used for the sample $\chi$ rotation. An example of such a system is the Bruker D8 ADVANCE with a ¼ circle Eulerian cradle option, and a 150 millimeter x-y mapping stage built onto the Eulerian cradle (Bruker 1997 Catalog Order No. B88-E00001). In this apparatus the x and y stages are mounted on top of a z stage (vertical linear motion), which is in turn mounted on top of a $\phi$ rotating stage. The entire combination of x, y, z, and $\phi$ stages are then mounted onto the ¼ circle (90°) Eulerian cradle to provide the sample $\chi$ rotation.

This mapping stage was built to handle semiconductor wafer diameters to 150 millimeter (6 inches). Such a stage could clearly be enlarged with proper design to handle wafers up to 200 millimeters or 300 millimeters in diameter. Diffraction systems built around this combination of wafer motion stages could also be set up to utilize an area x-ray detector such as HI-STAR. For example, the D8 ADVANCE with 150 millimeter wafer mapping and HI-STAR detector is commercially available. However, such a system would still exhibit several disadvantages. First, the total wafer motion control would be quite expensive in order to maintain wafer alignment, due to the use of the large Eulerian cradle which provides the sample $\chi$ rotation, in addition to supporting the other motion stages (x, y, z, and $\phi$). This is demonstrated by the present high cost of the current Bruker ¼ circle Eulerian cradle option with the built-in 150 millimeter x-y mapping stage. Making it large enough to handle 200 mm wafers (8 inches), or 300 mm wafers (12 inches) would only exacerbate that cost.

A second major drawback is the large clearance distance required between the area detector and the contemplated combination of sample motion stages. The area detector must be located relatively far from the sample in order to allow for rotational and translational freedom of all the sample motion stages. If the detector were placed too close to the motion stages, the sample (or motion stage) would collide with the detector at the sample's far range of travel. A large distance between the detector and measurement location on the sample results in a much smaller range of $\chi$ and $2\theta$ captured by the area detector at any one location. Thus more sequential angular locations are required to obtain texture information, and the measurement takes longer to carry out. In essence the system becomes more and more like a traditional four circle scanning diffractometer using a point detector, and less of the area detector advantage is capitalized upon. If the area detector is placed very close to the measurement point the angular range of $2\theta$ and $\chi$ covered by the detector will be quite large, however the motion of the wafer will be severely restricted resulting in highly truncated pole figures.

It therefore is an object of the present invention to provide a crystalline texture measurement system that operates rapidly; measures texture with a high degree of accuracy; is capable of taking texture measurements over the entire surface of large (e.g., 200 millimeter and 300 millimeter) semiconductor wafers; is amenable to automation; and can be operated by persons without extensive specialized skill and training.

It is another object of the present invention to provide quantitative texture information on a defined material present on a wafer (e.g., the metal interconnect on a semiconductor wafer) much more rapidly than is possible with any texture mapping system in the prior art.

It is still another object of the invention to provide a system enabling sufficiently rapid texture measurement to allow automated use of texture analysis in development and production quality control in commercial semiconductor processing operations.

A further object of the present invention is to provide texture mapping information anywhere on the surface of a wafer under test, even for very large (e.g., 200 millimeter and 300 millimeter) wafers.

A further object of the present invention is to provide texture mapping information with a high degree of resolution, preferably in steps of one degree or less in the $\phi$ and $\chi$ directions.

A further object of the present invention is to provide a texture mapping system that can be operated in a production environment, and by persons without specialized skilled or training.

Other objects and advantages will be more fully apparent from the ensuing disclosure and appended claims.

SUMMARY OF THE INVENTION

The present invention achieves the aforementioned objects through the use of an area x-ray detector; a unique set of wafer motions as compared to those employed in the prior art; a particular fixed special geometrical relationship between the x-ray beam source, the area x-ray detector, and the wafer under measurement; and a unique and innovative texture analysis protocol.

This combination of features provides more texture information anywhere on a full size semiconductor wafer in far less time, using less complex and less costly apparatus, and with a much higher degree of accuracy than the closest related current x-ray texture analysis apparatus.

The use of an area x-ray detector, as opposed to the point source detectors traditionally used for texture mapping, greatly reduces data acquisition time by capturing a relatively large range in the 2θ direction and $\chi$ direction. Multiple diffraction arcs can thus be captured in a single detector frame, both reducing data acquisition time and increasing accuracy.

The present invention utilizes a different set of wafer motions, as compared to current x-ray texture analysis apparatus, arranged in a different order to allow close positioning of an area x-ray detector to the sample. This enables a large range of 2θ and $\chi$ to be captured by the area detector while still allowing mapping over the full wafer surface.

Another feature of the present invention is that the x-ray beam source and area x-ray detector are arranged in carefully chosen fixed spatial locations (thus fixed ranges of 2θ and $\chi$) that are optimally integrated with the particular set of wafer motions used, and optimally integrated with a primary set of materials that the inventive system is used to analyze. This enables the elimination of the Eulerian cradle and the θ–2θ rotating stages, as required in the prior art systems to fully map the wafer. Elimination of these motion stages greatly simplifies the system, significantly reducing its cost.

Still another feature of the present invention is the utilization of a texture analysis protocol that simultaneously analyzes the diffraction information from all the reflections captured within the detector area. This enables fine meshing of the $\phi$ and $\chi$ angles, and determination of the ODF value and volumetric fractions of texture components from truncated pole figures. This texture analysis protocol significantly increases the efficient use of a 2-D area x-ray detector for texture mapping on semiconductor wafers, and thus significantly decreases data acquisition time. It also enables a quantitative texture analysis on materials exhibiting sharp textures. The new analysis protocol itself can be extended to any type of texture analysis that utilizes a x-ray area detector, and is not limited to semiconductor wafer mapping.

All of these features are combined in a very specific manner in the apparatus and method of the present invention to obtain the optimum performance of the total system. The invention enables fast, efficient mapping of texture anywhere on typical semiconductor wafers combined with a high precision quantitative texture analysis, which no other system currently offers.

BRIEF DESCRIPTION OF THE DRAWINGS

Figure 10A:
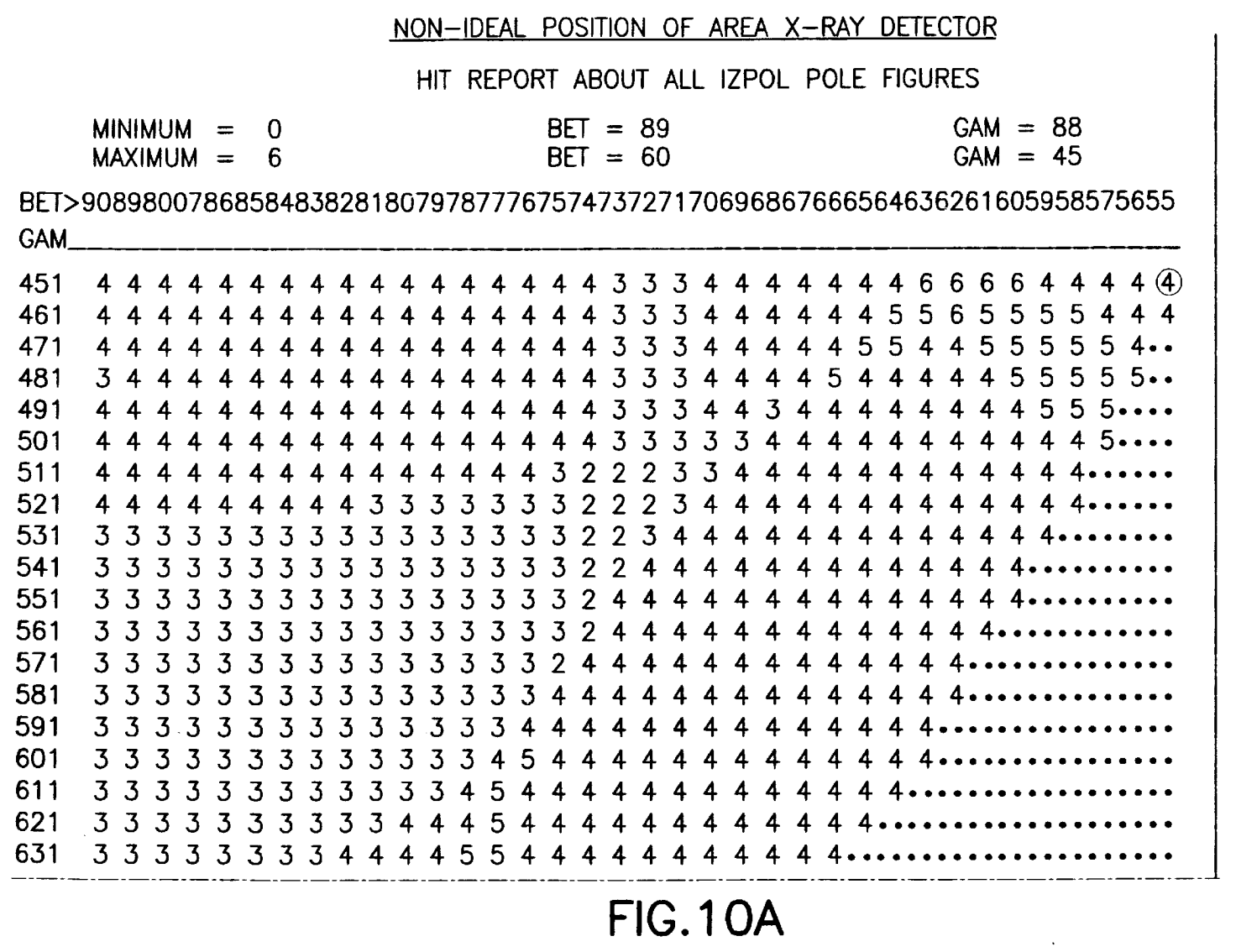
Figure 10B:
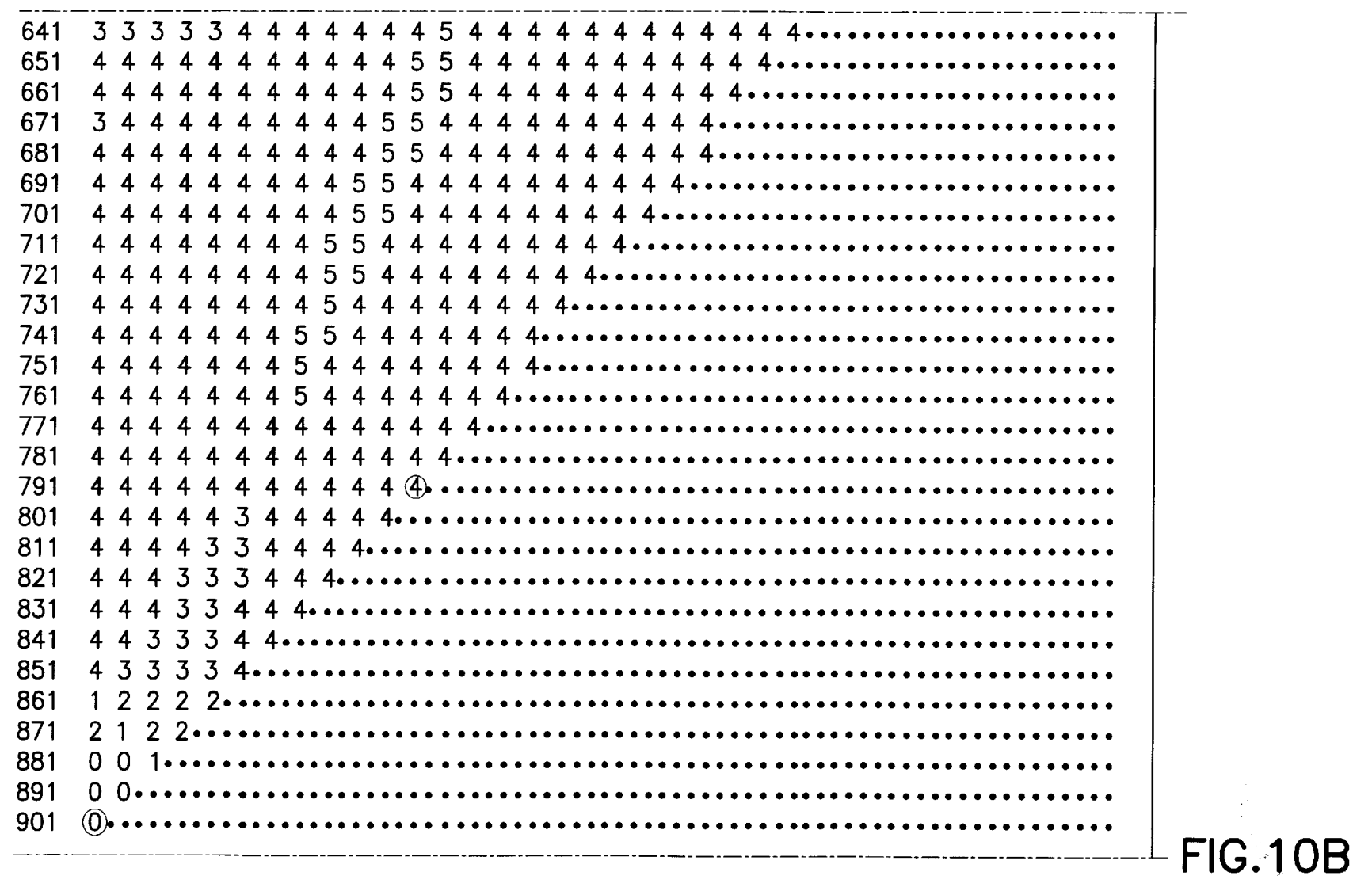
Figure 10D:
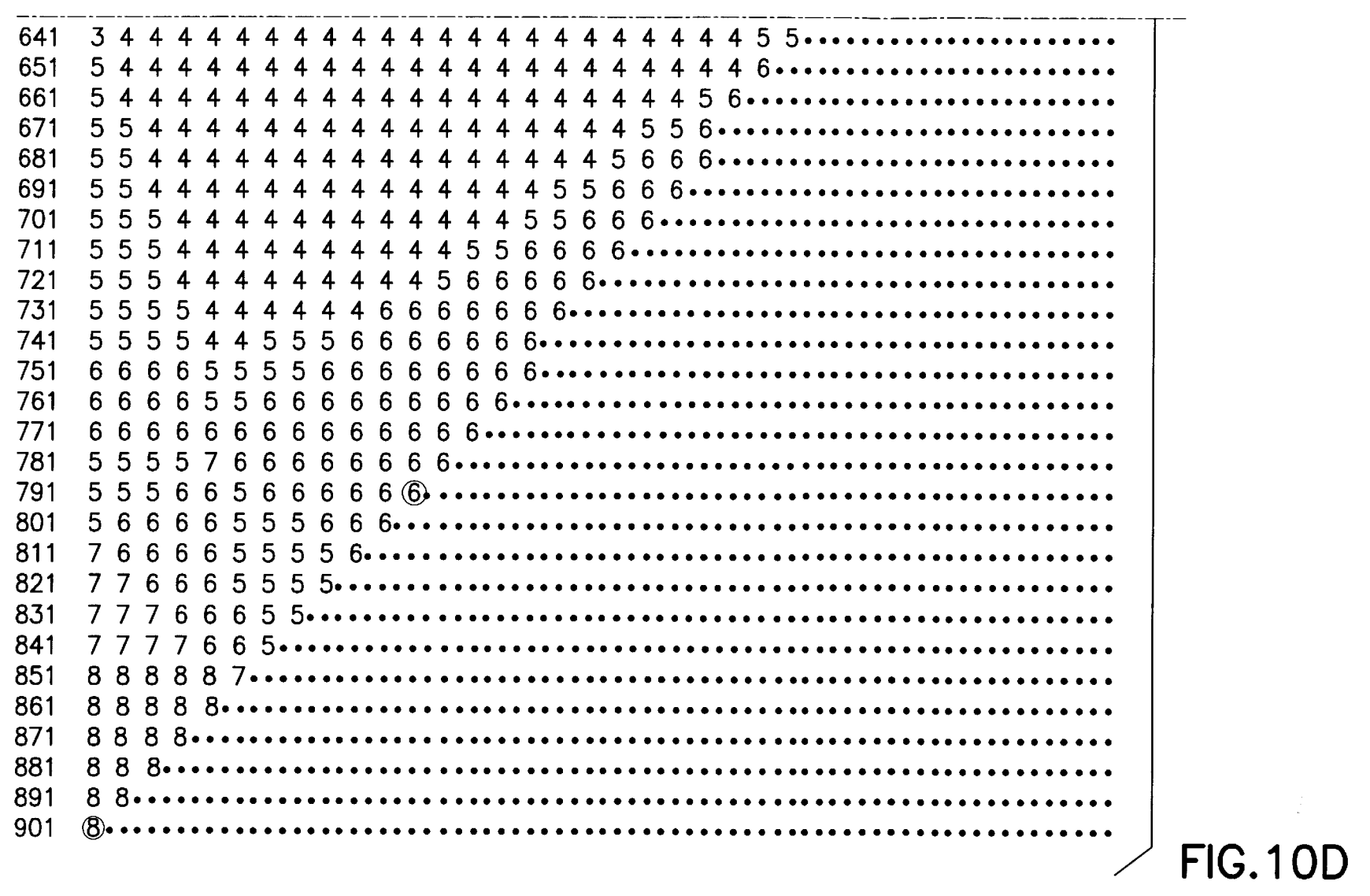

FIGS. 10A–D depicts examples of minimum pole density sets analysis for textures typical of metallization, including a non-ideal geometry and a preferred geometry optimized for copper film.

DETAILED DESCRIPTION OF THE INVENTION, AND PREFERRED EMBODIMENTS THEREOF

Figure 1:
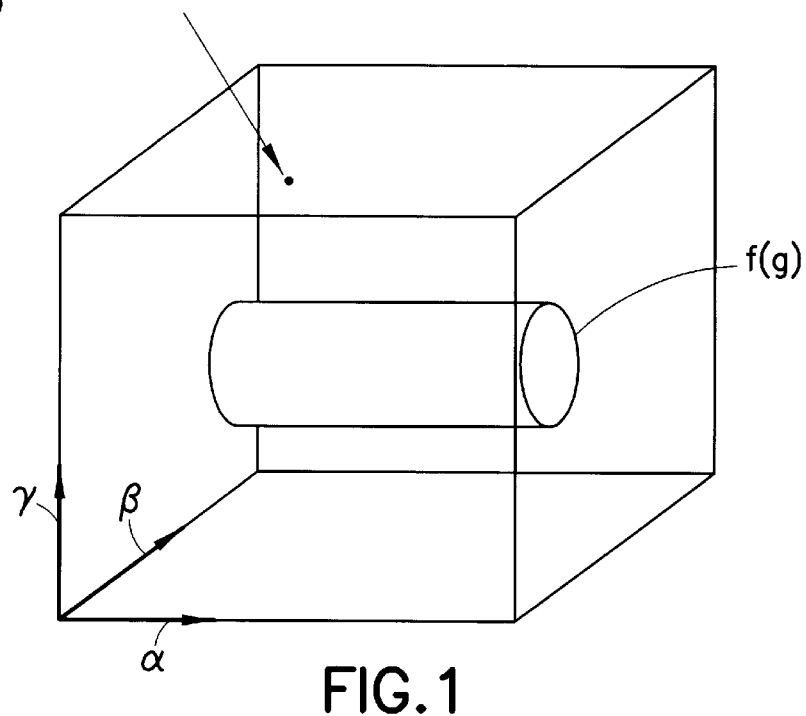
FIG. 1 is a schematic representation of the G-space of the Orientation Distribution Function, the quantitative measure of crystallographic texture.
Figure 2:
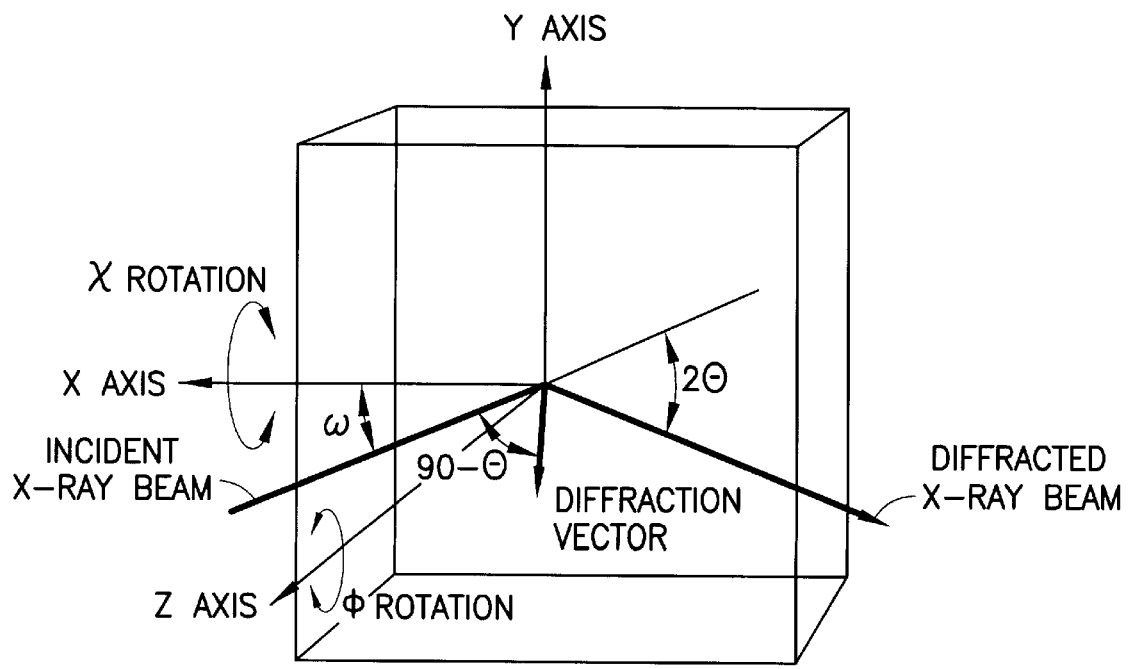
FIG. 2 depicts the relationship of sample rotation directions and the diffraction vector, according to the constant diffraction vector method of pole figure measurement.
Figure 3:
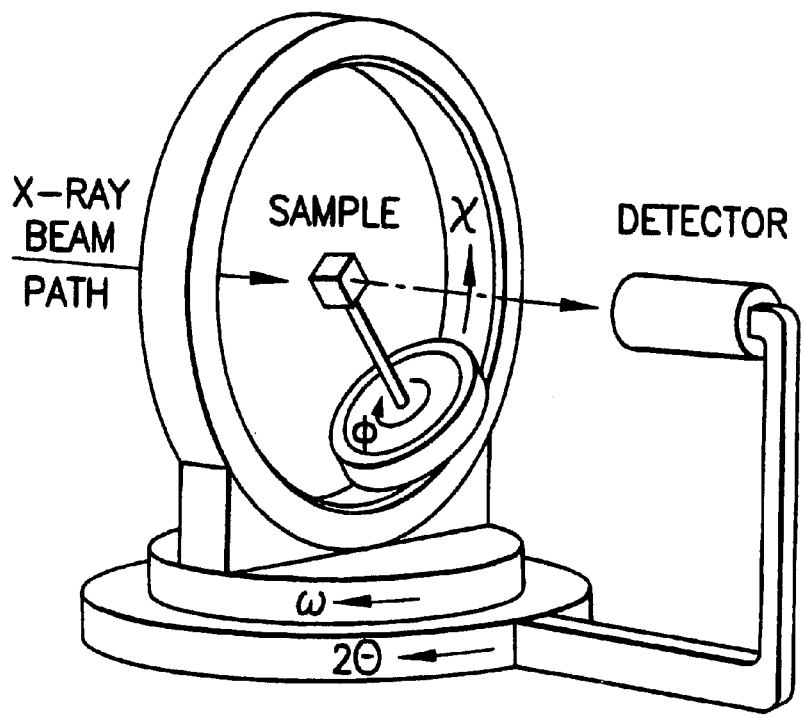
FIG. 3 depicts a four axis goniometer, a typical texture measurement apparatus of the prior art.
Figure 4:
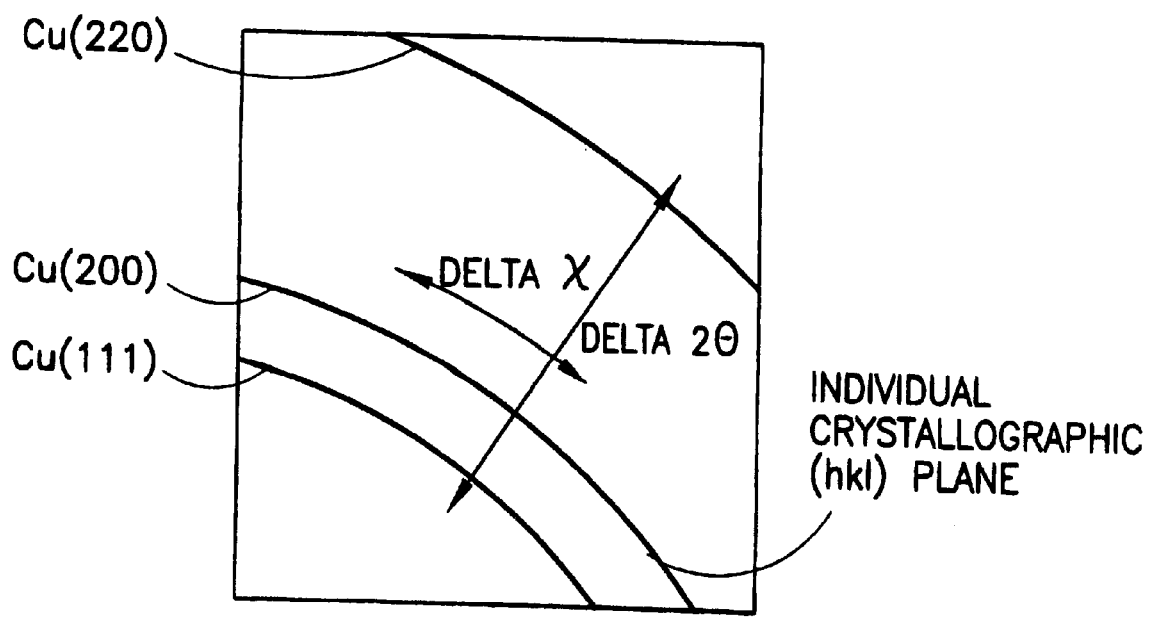
FIG. 4 is a single collection frame from an area x-ray detector, showing the diffraction peak arcs corresponding to three crystallographic planes of copper thin film.
Figure 5:
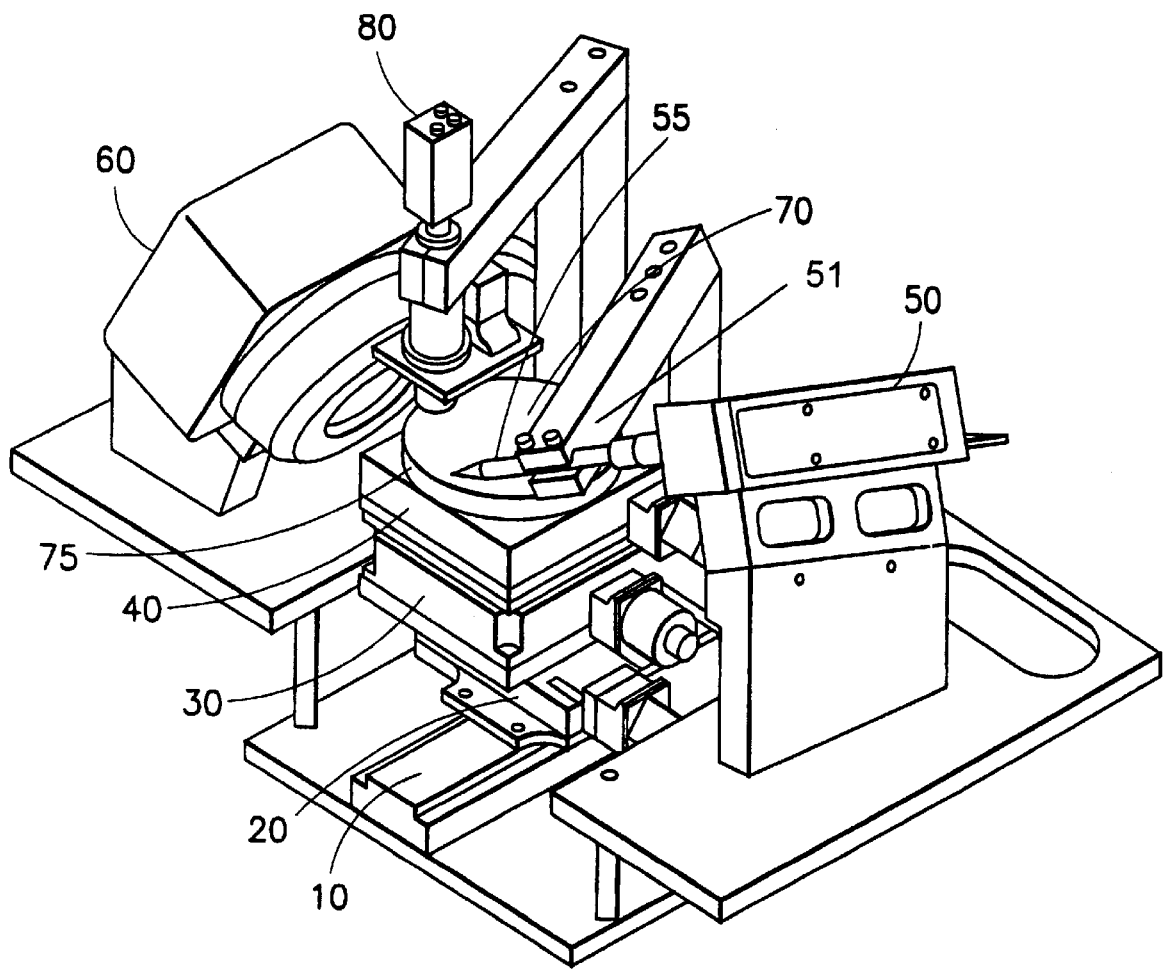
FIG. 5 is a perspective depiction of the essential components of the apparatus of the present invention, and of their spatial arrangement.

The present invention relates to an apparatus and method of measurement enabling fast texture analysis at any location on typical 200 millimeter semiconductor wafers. The invention could easily be extended to larger (such as 300 millimeter diameter) or smaller size wafers, and non-semiconductor applications. The apparatus and method of the invention combine the use of three critical items: (1) an area x-ray detector with its positioning optimized for speed and precision, (2) a specific set of limited wafer motions, and (3) a new high resolution texture analysis protocol that is optimized for the area detector, the particular set of chosen wafer motions, and a specific set of materials to be analyzed. A general schematic of the hardware layout of the invention is shown in FIG. 5.

The apparatus comprises three major interacting components: the x-ray source components, the wafer motion apparatus, and the detector. The x-ray area detector 60 is mounted to a rigid base. Also mounted to the rigid base is the sealed x-ray beam source 50, monochromator 51, and x-ray collimator 55, and the wafer motion apparatus, comprising a y-stage 10, an x-stage 20, a z-stage 30, and a φ-stage 40. Also shown is an optional video microscope 80. The system is primarily designed to handle semiconductor wafers up to 200 millimeters in diameter, but the apparatus can be readily modified to handle larger or smaller wafers 70.

A critical aspect of the invention is that it fixes the x-ray source and detector in specific spatial locations, and in a preferred embodiment makes use of four specific wafer motion stages, also in critical locations. The wafer motion stages are arranged in the following order from top to bottom: φ rotation, z (vertical) motion, x linear motion, and y linear motion. These wafer motions are configured in such a way as to allow nearly full wafer motion, as well as close proximity of the area detector to the wafer measure point 75.

Although described hereinafter with reference to a preferred embodiment of the invention wherein a sample motion assembly comprising three mutually orthogonal rectilinear translational motion stages operatively coupled to a rotational motion stage, it will be appreciated that the invention may be advantageously practiced with other sample motion-effecting means, such as sample translation robots, dynamic motion support structures, etc. which provide appropriate nature and extent of movement of the sample for texture analysis.

The sample motion-effecting means effectuate planar motions—movements in the plane of the sample. The sample is in the form of a thin wafer or other planar structure, and thus defines a corresponding sample plane. The movements of the sample for the texture analysis are in this sample plane, and the sample is not rotated out of the sample plane for the texture analysis; rather, all sample movements are "in-plane" movements, as effected by the sample motion assembly.

The apparatus of the present invention thus dispenses with the Eulerian cradle providing χ rotation, and the θ–2θ goniometer, of prior art texture analysis systems. These motion stages force the area detector to be placed at a larger distance from the measurement spot, to enable full motion of the wafer. This increased distance results in slower analysis, with more sequential rotations, and much less angular range of χ and 2θ at each detector position. The added stages also considerably increase the cost and complexity of wafer motion.

Arranging the x-ray source 50 and detector 60 at a fixed geometric location in the practice of the present invention does reduce the total observable range of 2θ and φ, since the detector 60 cannot be moved. However, it allows the detector 60 to be positioned much closer to the measurement point 75 on the wafer 70 under test. This allows for a much greater range of 2θ and χ within the detector area, and therefor fewer required sequential detector rotations. By optimizing the analysis protocol and limiting the system to analysis of a certain class of materials, complete texture information can be obtained without the additional detector rotation required in the 2θ and χ directions.

In the present invention the fixed range of 2θ and χ are optimized for a specific material system, by placing the detector 60 and x-ray source 50 at very specific permanent locations. By capturing a desired set of crystallographic reflections over a preferred range of χ for each reflection, the maximum amount of texture information can be extracted from the measurement process through a new and more efficient type of texture analysis. This new texture analysis protocol is part of the present invention. It is used to make most efficient use of the area detector 60, and to compensate for the exclusion of the 2θ and χ motions of the present apparatus. The result is much faster texture analysis with fewer and less complex wafer motions required. This analysis determines the ODF and volumetric fractions of texture components from several partial (severely truncated) pole figures.

The texture analysis is performed by a texture analysis processor which may comprise a computer, central processing unit (CPU), microprocessor, integrated circuitry, computational module, or the like, which is constructed, operated and arranged to determine and enable output of texture data by the texture analysis protocol from the diffraction characteristics of the detected diffracted energy. The texture analysis protocol may be embodied in any suitable form, such as software operable in a general purpose programmable digital computer. Alternatively, the protocol may be hard-wired in circuitry of a microelectronic computational module, embodied as firmware, or available on-line as an operational applet at an Internet site for texture characterization of the sample.

The sample may be of any suitable type, typically being generally planar to define an associated plane of the sample ("sample plane") within which the sample movements take place in the diffraction data generation operation. The movements take place "in plane" with reference to the sample plane, and in contrast to prior art methodologies no rotation "out of plane" is required.

The location of the x-ray source 50 and detector 60 is intimately related to the size, orientation, position and order of the motion stages, and to the primary material to be analyzed. The position of the x-ray source 50, detector 60 and motion stages are in turn intimately related to the specific texture analysis protocol to be used. Thus, the texture analysis protocol permits the fixed spatial relationship between the detector and the source to be determined, and the fixed angles employed to be optimized, thereby using the texture analysis protocol to design the diffractometer.

As an example of one preferred embodiment of the invention, the apparatus and its arrangement are shown for copper texture analysis on 200 millimeter wafers. Copper is a new interconnect material that the semiconductor industry is rapidly adopting for high-speed integrated circuits. The $\chi$ rotation and the $\theta$–$2\theta$ motions are eliminated in the present invention. This greatly simplifies the system for large wafer mapping, but it also limits the total range in $\chi$ and $2\theta$ that the detector covers. The x-ray source 50 and detector 60 are placed in specific geometrical locations so as to capture an optimized range of $\chi$ and $\theta 2\theta$. For copper, the Cu (111) reflection at $2\theta=43.3°$, the Cu (200) reflection at $2\theta=50.4°$, and Cu (220) at $2\theta=74.1°$ are sufficiently close in 2 to be collected in a single detector frame of the HI-STAR detector, and are of relatively strong intensity for texture analysis using the same HI-STAR detector. Reflections occurring at higher $2\theta$ values have much lower intensity for thin semiconductor coatings, and require long collection times in order to achieve meaningful counting statistics.

It is advantageous to position the area x-ray detector 60 as close to the measurement spot 75 on the wafer 70 as possible, while maintaining sufficient angular resolution, and sufficient clearance from the wafer motion stages at their closest position to the detector. The measurement spot 75 is a fixed position in space that all components (wafer 70, detector 60, and x-ray source 50) are aligned to. It is the actual diffracting volume on the sample. While the motion stages move different locations on the wafer to the measurement spot, the measurement spot itself does not move, rather it is fixed at one location in space. The elevation or "z" position of the top surface of the wafer is always fixed at the same value so the wafer only moves in the x-y (horizontal) plane. The z axis stage 30 is only used to ensure that the measurement point 75 can always be kept at the same vertical position regardless of wafer thickness. The optimal $2\theta$ range for the copper (111) (200), and (220) reflections is approximately 38° to 80°. The minimum detector 60 distance from the measurement spot 75 is limited by the size of the wafer itself. For example a 200 millimeter prevents the HI-STAR area detector from being placed any closer than ~12 centimeters from the centerpoint of the wafer. This is shown schematically in FIG. 6. In practice, part of the area detector 60 drops below the plane of the wafer, since the preferred reflections occur at lower $2\theta$ angles, and the overall size of the detector 60 is usually much larger than the active detector area 65 (at least in the case of the HI-STAR detector).

The choice and order of wafer motion stages is critical in order to place the detector close to the measurement point. The requirement for this apparatus is to perform texture analysis at any location on the wafer 70 at the measurement spot 75, and to be able to rotate the wafer in the $\phi$ direction at that measurement spot. The $\phi$ rotation means rotating in the plane of the wafer. By stacking two perpendicularly oriented linear stages with a rotary stage, all positions on the wafer can be reached at all $\phi$ rotations. It is common practice in industry to place the x and y linear motions on top of the $\phi$ rotary motion stage. The center of rotation of the $\phi$ rotary stage is normally aligned directly underneath the measurement spot. In such a configuration, any position on the wafer can be reached with the x-y stages, and that position will remain in the beam path (at the measurement spot) during $\phi$ rotation, since the center of the $\phi$ rotary motion is always below the measurement spot. The drawback to stacking the x and y stage on top of the rotary stage is the large required distance between the detector and the measurement spot, which significantly reduces the $\chi$ and $2\theta$ range captured by the detector. This is due to the large swing radius resulting from an extended linear stage effectively enlarging the radius of the rotary stage on which it sits.

In the practice of the present invention the rotary stage 40 is placed on top of the x and y linear stages (20 and 10, respectively), rather than below them. The total $\phi$ rotation range is also restricted to 180° rather than the full 360°. This configuration allows the area detector 60 to be positioned as close to the measurement point 75 as possible, while still achieving a large degree of wafer motion. This is contrary to the practice used in recent commercial x-ray texture mapping apparatus. By placing the rotary stage on top of the x-y stage combination, the swing radius is never larger than the size of the rotary stage itself, and the detector can be positioned closer to the measurement spot 75. With this arrangement the center of rotation of the $\phi$ rotary stage 40 is not always under measurement spot 75. Thus, in order to measure different $\phi$ angles at a particular location on the wafer, x and y translation motions must be used in combination with each $\phi$ rotation. For example, at any location on the wafer 70 other than its center, every time $\phi$ is changed the wafer location will translate away from the measurement spot. A specific x and y translation can be used to return that location to the measurement spot without altering the $\phi$ angle to which that the sample was rotated.

Figure 7:
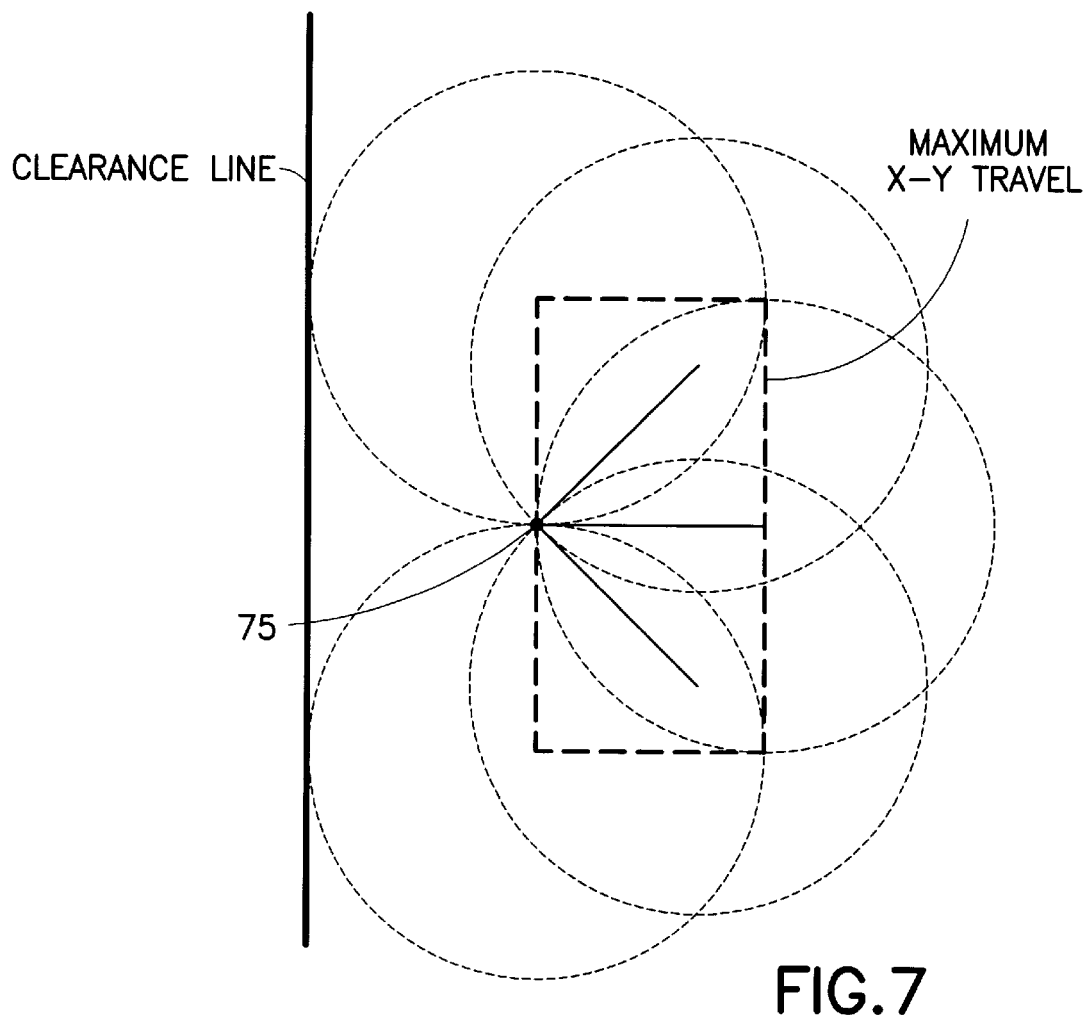
FIG. 7 is a schematic representation of the spatial relationship between a large wafer, as it is rotated and translated while maintaining a fixed measurement spot, and the limit of position of x-ray area detector.

This is schematically shown in FIG. 7, which depicts 180° of $\phi$ rotation at an extreme edge location of a wafer, while keeping the detector 60 close to the measurement spot 75. By limiting the total rotation range to 180° for any point on the wafer, the maximum horizontal displacement of the detector 60 from the measurement spot 75 is slightly greater than the wafer radius (i.e., just over 100 mm for a 200 mm diameter wafer). If a full 360° of rotation were used, the horizontal displacement of the detector 60 from the measurement spot 75 would need to be slightly greater than the full wafer diameter. Thus, the $\phi$ rotation is limited in the present invention to 1800 in order to keep the detector 60 closer to the sample 70.

However, each different radial position on the wafer 70 will result in a different 180° band of $\phi$ values between 0 and 360° (based on some reference zero position of $\phi$ on the wafer). With 180° of range in $\phi$ range, at least one full quadrant (90°) of a pole figure will be always be captured anywhere on the wafer 70. The minimum required range is 90° of 4 for cubic materials, which exhibit four fold symmetry.

Figure 6:
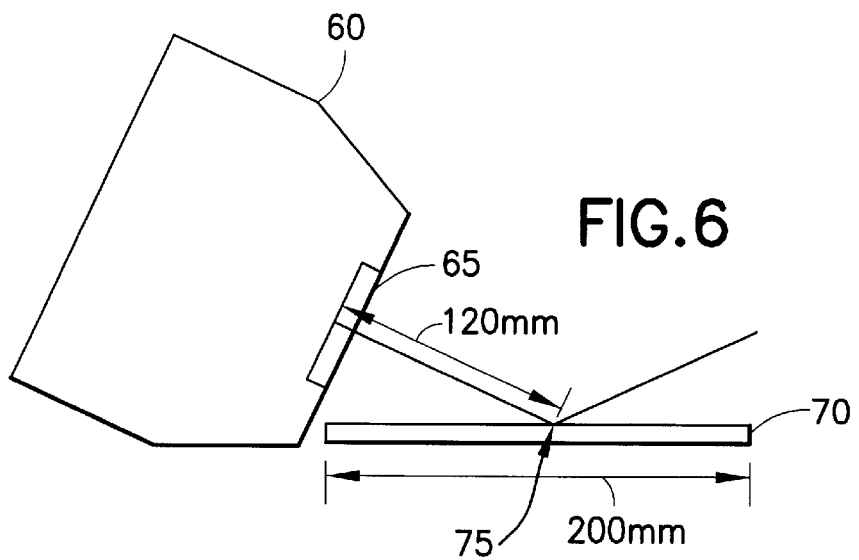
FIG. 6 is a schematic representation of the spatial relationship between the x-ray area detector and a 200 mm wafer according to one embodiment of the present invention.

In the preferred embodiment of the present invention, the optimal $2\theta$/ and $\chi$ range causes the example HI-STAR detector 60 to drop below the plane of the wafer 70 (as shown in FIG. 6). In order to keep the detector 60 as close to the measurement spot 75 as possible the amount of $\phi$ rotation for any wafer location (other than the wafer center point) is limited to 180° since the detector 60 falls below the plane of the wafer 70. The 180° rotation of $\phi$ is sufficient for texture analysis since the analysis algorithm according to the present invention takes advantage of sample and crystal symmetries.

The invention is also applicable to an area detector which is compact enough to be positioned completely above the wafer plane, and shaped in such a way as to capture an equivalent desired range of $2\theta$ and $\chi$. With such a detector, 360° of $\phi$ rotation would be possible. In such an arrangement it is also possible to mount the x and y linear stages above the rotary stage if so desired. The data acquisition method and texture analysis protocol of the present invention is applicable to such an area detector, which remains above wafer plane. No such area detector, of the proper size and shape, and possessing the necessary sensitivity, currently exists. In either case (detector above the wafer motion plane, or below it) the 2θ and χ motions are eliminated, the x-ray source and detector are set in fixed positions, and the same texture analysis protocol is used.

Using the described combination of motion stages (10, 20, 30, and 40) and fixed position of x-ray source 50 and area x-ray detector 60, the specific crystallographic reflections and range of χ capture can be optimized for the accuracy of the ODF reproduction. In the case of copper the Cu (111) reflection at 2θ= 43.3°, the Cu (200) reflection at 2θ=50.4°, and Cu (220) at 2θ=74.1° provide one example of three preferred reflections that can be observed by the HI-STAR area detector on a 200 millimeter wafer at a detector to measurement spot distance of 12 centimeters. Rather than locate the midpoint of the detector at the χ=0° location, the midpoint can be located at a non-zero χ value such that the range of χ covered by the detector is maximized for each of the observed crystallographic planes. If the detector can be placed sufficiently close to the measurement point 75, the χ range of the detector will cover the full 85° of χ that is typically used for a pole figure measurement. However, a large (e.g., 200 mm) semiconductor wafer prevents the detector 60 from being placed close enough to allow for a full 85° of χ to be captured at one detector position.

Figure 8:
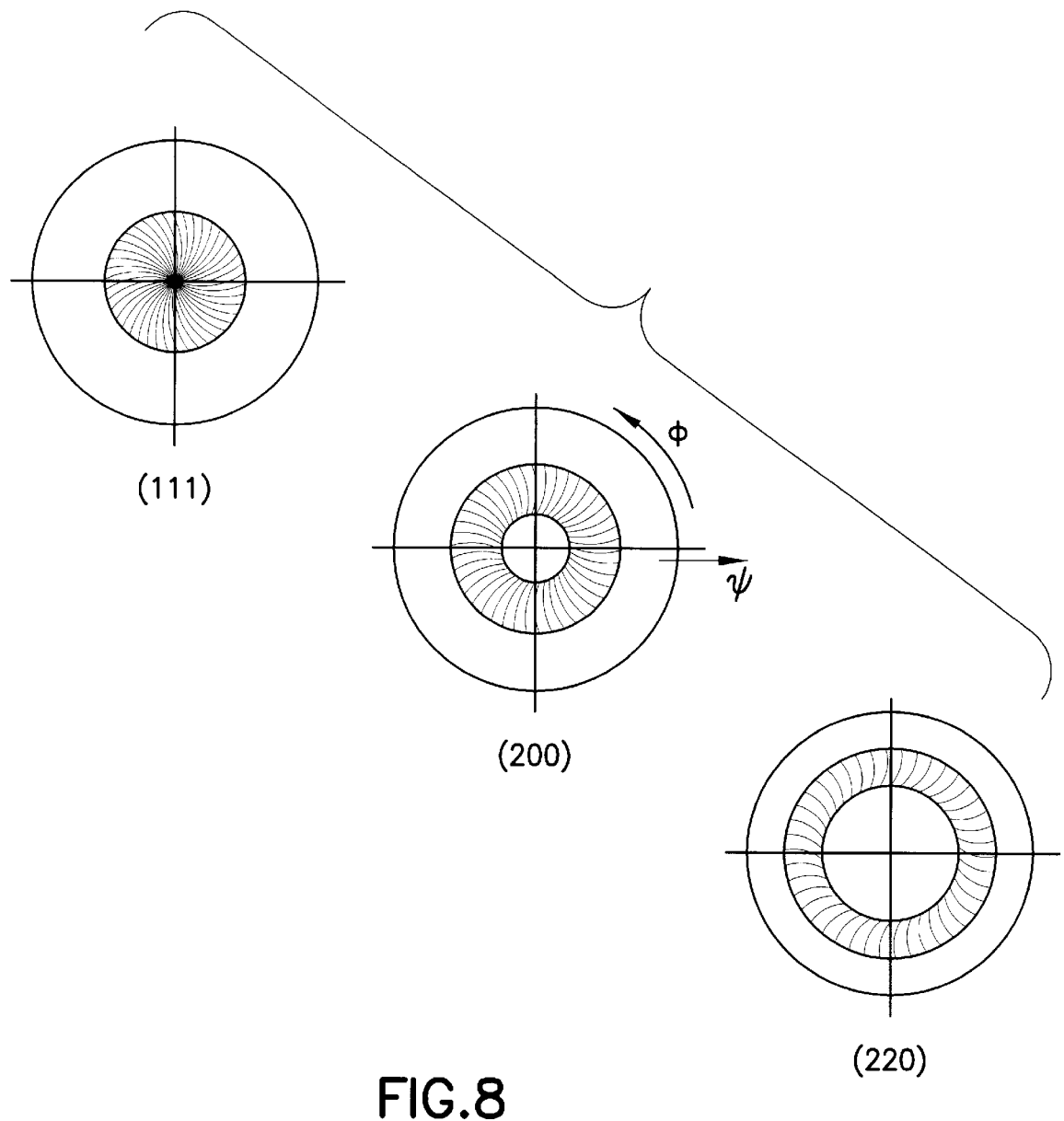
FIG. 8 depicts the sets of partial pole figures corresponding to three crystallographic planes, each curved line corresponding to one diffraction peak arc, three of which were captured in each x-ray area detector collection frame.

At a distance of 12 cm, the area detector covers a limited range of χ angles on each pole figure. This results in truncated pole figures, as schematically shown in FIG. 8. In FIG. 8 each curved line represents data from one diffraction arc of a crystallographic reflection on the area x-ray detector. Each detector collection frame contains one diffraction arc for each of the (111), (200), and (220) reflections. With these partial pole figures, reproduction of the ODF may be impossible or of poor accuracy and precision. However, blanket semiconductor metallization films or patterned metallization structures typically have an axial cyclic fiber (ACF) texture, wherein each crystallite, or grain, has the same particular crystallographic orientation parallel to a particular direction on the sample (for example the direction normal to the sample surface) and is randomly rotated around this axis. For the case of copper blanket films deposited on a silicon wafer the grains may typically have a (111), (511), or (100) cyclic fiber texture. For a cubic material such as copper, the ACF-ODF contains about 3000 nonequivalent 1-degree cells (unknowns). The 3 incomplete pole figures contain approximately 144 cells (knowns) so the reproduction of the true ODF is a non-trivial effort.

Figure 9:
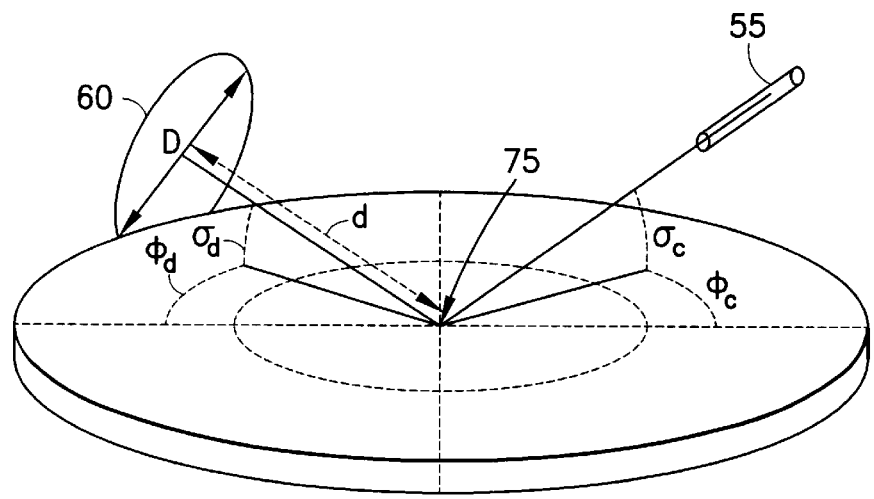
FIG. 9 is a schematic representation of the geometry of the x-ray source, a sample under measurement, and an area x-ray detector.

The regions covered on each pole figure (i.e., the number and location of cells) depend on the geometry of the x-ray source-sample-detector. This geometry is shown in FIG. 9. The polar angles $\sigma_c$, $\phi_c$ determine the position of x-ray source, the angles $\sigma_d$, $\phi_d$ determine the position of the detector, d is the detector to sample distance, and D is the detector diameter.

The geometry is described by 6 parameters: 2 polar angles for x-ray collimator, 2 polar angles for the detector, and detector radius and distance to sample. Those 6 parameters are optimized in such a way that the regions covered on 3 pole figures provide the necessary and sufficient data for the reproduction of the ODF.

Figure 11:
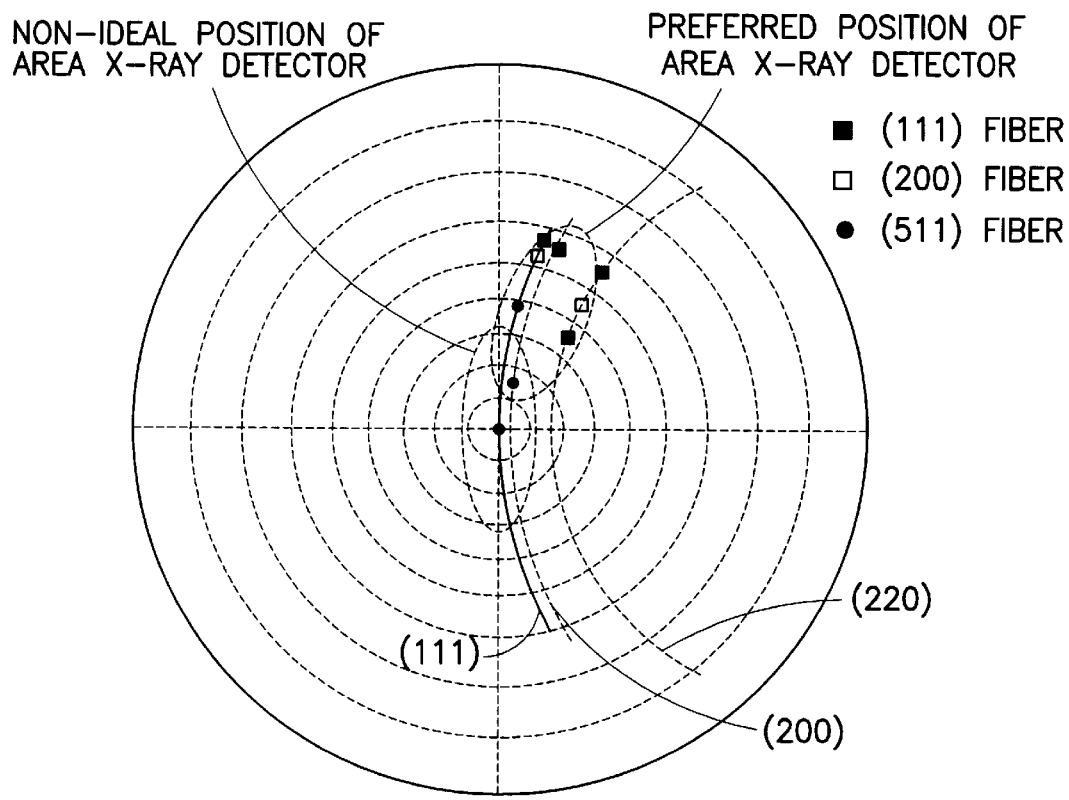
FIG. 11 is a projection in the pole figure space of the linear cross sections through three pole figures with locations corresponding to specific copper cyclic fiber textures, and the projection of the detector area.

Two criteria are considered:

MPDS (multiple pole density set) is a necessary condition that every single orientation must be determinable (K. Helming, "Minimal Pole Figure Ranges for Quantitative Texture Analysis," Textures and Microstructures, 19 (1992) 45–54). FIGS. 10 and 11 show examples of such an analysis.

FIG. 10 represents an α=const. cross-section of an ODF (all the α-cross-sections are the same for fiber textures). The numbers at each β-γ coordinate location correspond to the amount of information at this particular location provided by the experimental pole figures. The higher numbers mean higher importance. Two cases are shown, a non-ideal geometry, and a preferred geometry optimized for copper films. FIG. 11 is a stereographic projection of the linear cross-sections through (111), (200), and (220) pole figures with the locations corresponding to (111), (511), and (100) cyclic fiber textures marked on them, and the projection of the detector area on that stereographic projection. FIG. 11 shows the projection of the area x-ray detector for the same non-ideal location and the preferred position described in FIG. 10. For the reproduction of the ODF the detector must cover the projections of the essential texture components of interest. FIGS. 10 and 11 shows that the preferred position of the area detector is essentially that position where the detector can capture the {111}, {200}, and {511} fibers.

The detector and x-ray beam incident angles (see FIG. 9) for the non-ideal case and preferred case are as follows:

Non-ideal ($\sigma_c$=21.6°, $\phi_c$=0°, $\phi_d$=21.6°, $\phi_d$=0°)

Preferred ($\sigma_c$=17.2°, $\phi^c$=0°, $\phi_d$=26.6°, $\phi_d$=35°)

Errors between the true and reproduced pole figures must be within acceptable limits or the proposed method of generating the ODF from truncated pole figures will not be effective. The textures found in thin metal films and discrete interconnects have been simulated by sets of model textures. The variables were the texture type, its volumetric fraction, and sharpness. The model ODFs and pole figures were then constructed. Subsequently the pole figures were "truncated" in such a way as to simulate the experimentally available truncated pole figures (which is a function of measurement geometry as previously described). The ODF and complete pole figures then were recalculated and the relative error between the original and recalculated ODFs and pole figures was determined as follows:

$$RO(\varepsilon) = \frac{1}{N}\sum_{n=1}^{N}\frac{|ODF_n^{cal} - ODF_n^{mod}|}{ODF_n^{mod}}100\%$$

$$RP(\varepsilon) = \frac{1}{IJ}\sum_{i=1}^{I}\sum_{j=1}^{J}\frac{|PF_{ij}^{cal} - PF_{ij}^{mod}|}{PF_{ij}^{mod}}100\%$$

wherein:

$ODF_n^{cal}$—ODF values recalculated from truncated pole figures $ODF_n^{mod}$—ODF values of model textures $PF_{ij}^{cal}$—pole figure values calculated from $ODF^{cal}$ $PF_{ij}^{mod}$—pole figure values of model textures i—indicates the pole figure (I is the number of pole figures taken to ODF calculation, in this case I=3)

j—indicates the point on pole figure (J is the number of points on pole figures taken to calculation)

n—indicates the point in orientation space (N is the number of ODF calculated points)

ε—indicates the value level above which the ODF or PF values are taken in the calculation of RO or RP respectively.

The minimization of those errors was done in terms of the x-ray source-sample-detector geometry i.e., the areas covered on each pole figure.

An illustrative texture is composed of 30% random, 50% of (111) fiber, 10% of (100) fiber, and 10% of (511) fiber. All fiber texture components are modeled by Gaussian functions with full width half maximum of 10°. A 5°×5° mesh was used for pole figure simulation and ODF calculations. Considering 6 geometries (Case 1 to Case 6) of measurement resulting in different coverage of experimental pole figures, one obtains:

| Pole Figure | Range of $\chi$ | | | | | |
|---|---|---|---|---|---|---|
| | Case 1 | Case 2 | Case 3 | Case 4 | Case 5 | Case 6 |
| (111) | 0°–60° | 5°–65° | 10°–70° | 15°–75° | 20°–80° | 25°–85° |
| (200) | 5°–55° | 10°–60° | 15°–65° | 20°–70° | 25°–75° | 30°–80° |
| (220) | 15°–50° | 20°–55° | 25°–60° | 30°–65° | 35°–70° | 40°–75° |

The relative errors in ODF and pole figure determination are as follows:

| Relative error | Case 1 | Case 2 | Case 3 | Case 4 | Case 5 | Case 6 |
|---|---|---|---|---|---|---|
| RO(0.0) | 11.8 | 12.7 | 15.1 | 13.9 | 13.2 | 19.5 |
| RO(0.3) | 11.6 | 12.8 | 15.0 | 13.8 | 13.6 | 20.4 |
| RP(0.0) | 5.7 | 4.5 | 4.2 | 4.1 | 3.7 | 3.0 |
| RP(0.3) | 6.1 | 4.5 | 4.2 | 4.1 | 3.7 | 3.0 |

Case 1 provides for the optimal measurement geometry with which the ODF will be reproduced with approximately 12% error, and individual pole figures will be reproduced with error of 6%.

High accuracy of texture determination requires that the pole figures be measured with the highest possible accuracy and with high resolution in pole figure angles $\chi$ and $\phi$. The GADDS area x-ray detector has a sufficiently high resolution in $2\theta$ and $\chi$ (approximately 0.15 degrees). The angular resolution of the second pole figure coordinate ($\phi$) depends on the step in $\phi$ of the sample rotation. This step may be selected by moving the rotary stage (which has the minimum step of 0.002 degrees) in such a way that the resolution of 0.15 degrees is achieved in $\phi$. At present, the resolution of 1 degree is sufficient for thin films, but higher resolution may be required in the future.

The texture output data relevant to most users such as complete pole figures, line plots (one dimensional section through a pole figure), and volumetric fractions of texture components cannot be elucidated directly from several incomplete pole figures registered by the detector. First, the ODF must be calculated from truncated pole figures. The three dimensional distributions of grains in polycrystalline aggregates can be calculated from two-dimensional projections of ODF (pole figures) by means of direct pole figure inversion or by series expansion methods. The series expansion methods {(H. J. Bunge, Texture Analysis in Materials Science (Butterworths, London, 1982)), (R. J. Roe, "Description of crystalline orientation in polycrystalline materials. (III) General solution to pole figure inversion," J. Appi. Phys. 36 (1965), 2024–2031)}, and the series expansion method using Gauss-type model functions (K. Lucke, J. Pospiech, and J. Jura, Z. Metallkunde 77(1986), 312) have instrinsic truncation errors and are not suited for analyzing sharp textures (W. Truszkowski, J. Pospiech, T. Pawlik, "Rolling Texture of Silver Single Crystals Described by the Descrek Orientation Distribution, ICOTOM 8, ed. J. S. Kallend & G. Gottstein, TMS, P 531–536, 1988). The direct methods, including the vector method (D. Ruer and R. Barro, Adv. X-ray Anal. 20 (1977), 187), the Imhof method (J. Imhof, Textures and microstructures, 4 (1982), 189), the WIMV method (S. Matthies, "On the reproducibility of the orientation distribution function of texture samples from pole figures (ghost phenomena), Phys. Stat. Sol. (b) 92 (1979), K135–K138), and the ADC method (K. Pawlik, Phys. Stat. Sol. (b) 124 (1986), 477) lead to errors caused by the under-determination of the set of linear equations relating discrete cells in pole figures to cells in the three-dimensional orientation space. In the case of sharp textures the ADC and WIMV methods work the best (D. Raabe and K. Lucke, "Analysis of the ADC Method for Direct ODF Calculation by Use of Gauss Models and Standard Functions," Materials Science Forum 157–162 (1994) 413–418).

Figure 12:
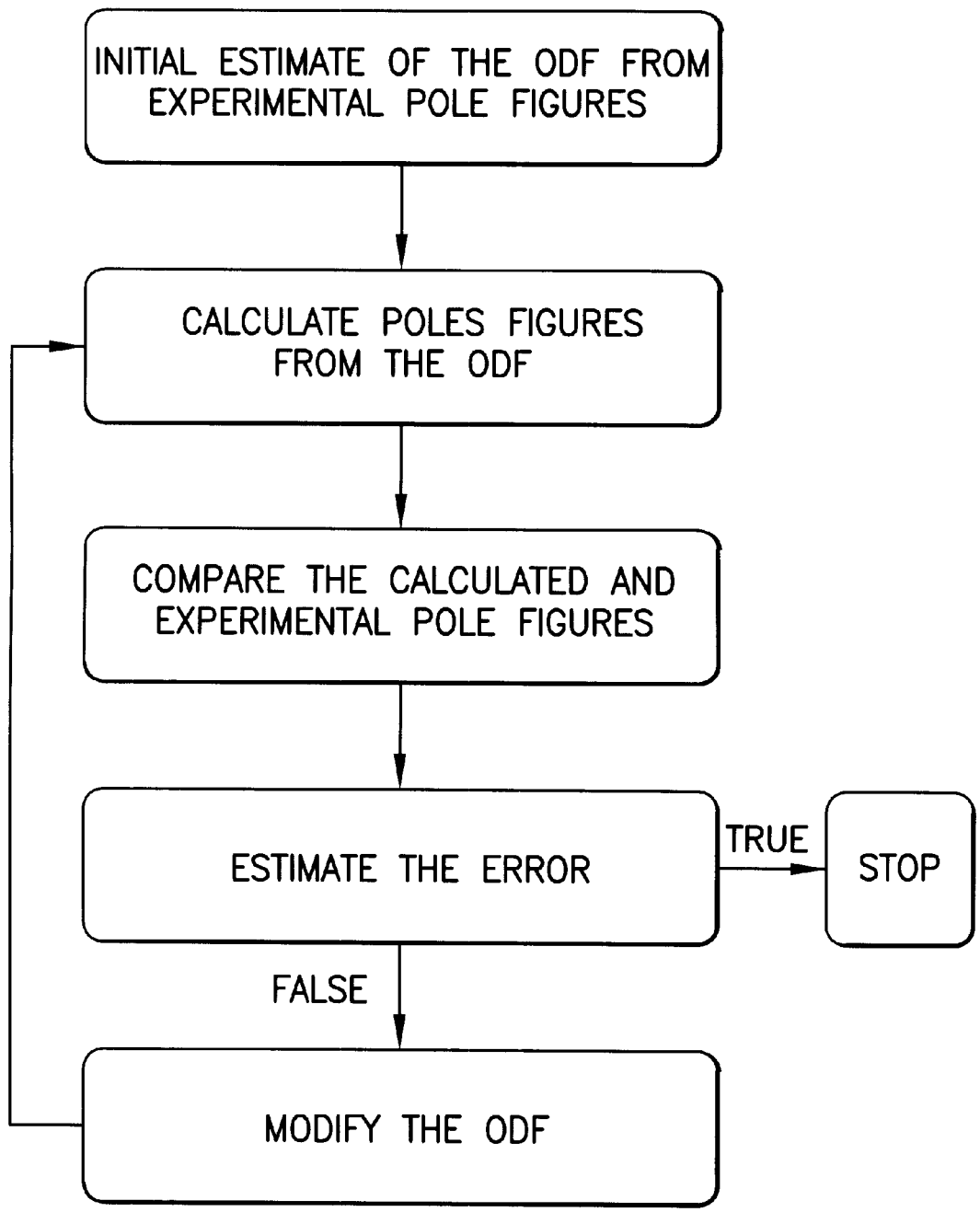
FIG. 12 is a flowchart depicting the ODF calculations, according to one embodiment of the present invention.

The ODF calculation protocols utilizing an arbitrary step resolution (e.g., 1, 2, 3, and 5 degrees) and optimized for cyclic fiber texture have been developed and are part of the present invention. Two approaches were used: the modified WIMV method (S. Matthis and G. W. Vinel "On the reproduction of the orientation distribution function of texturized samples from reduced pole figures using conception of a conditional ghost correction," Phys. Stat. Sol. (b) 112 (1982), K111–120) and the arbitrary defined cell method (ADC) (K. Pawlik, Phys. Stat. Sol. (b) 124 (1986), 477). The flow chart for the ODF calculations is shown in FIG. 12.

Figure 13:
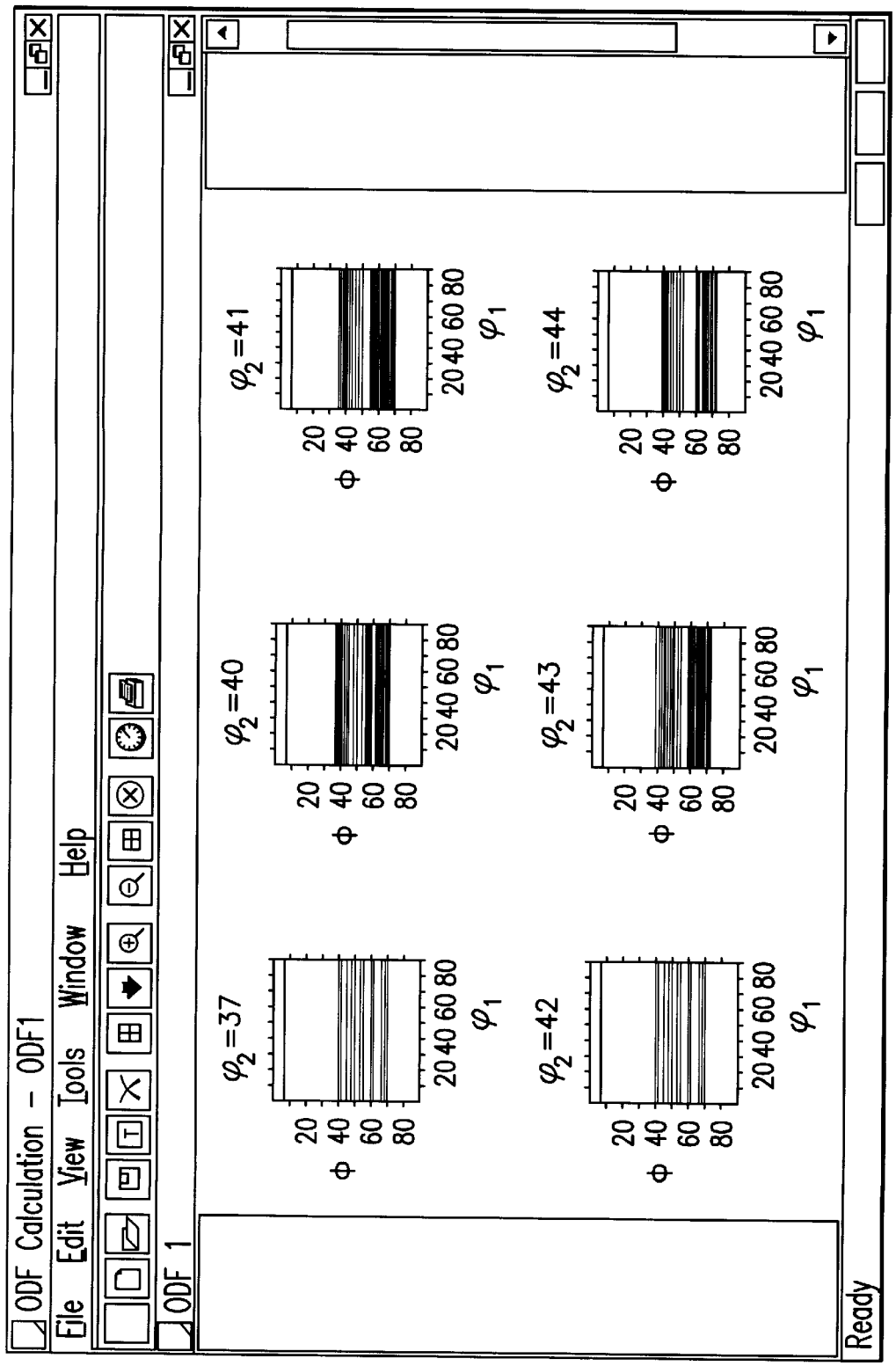
FIG. 13 shows an example of an ODF calculation with one degree resolution for a copper interconnect with fiber textures.
Figure 14:
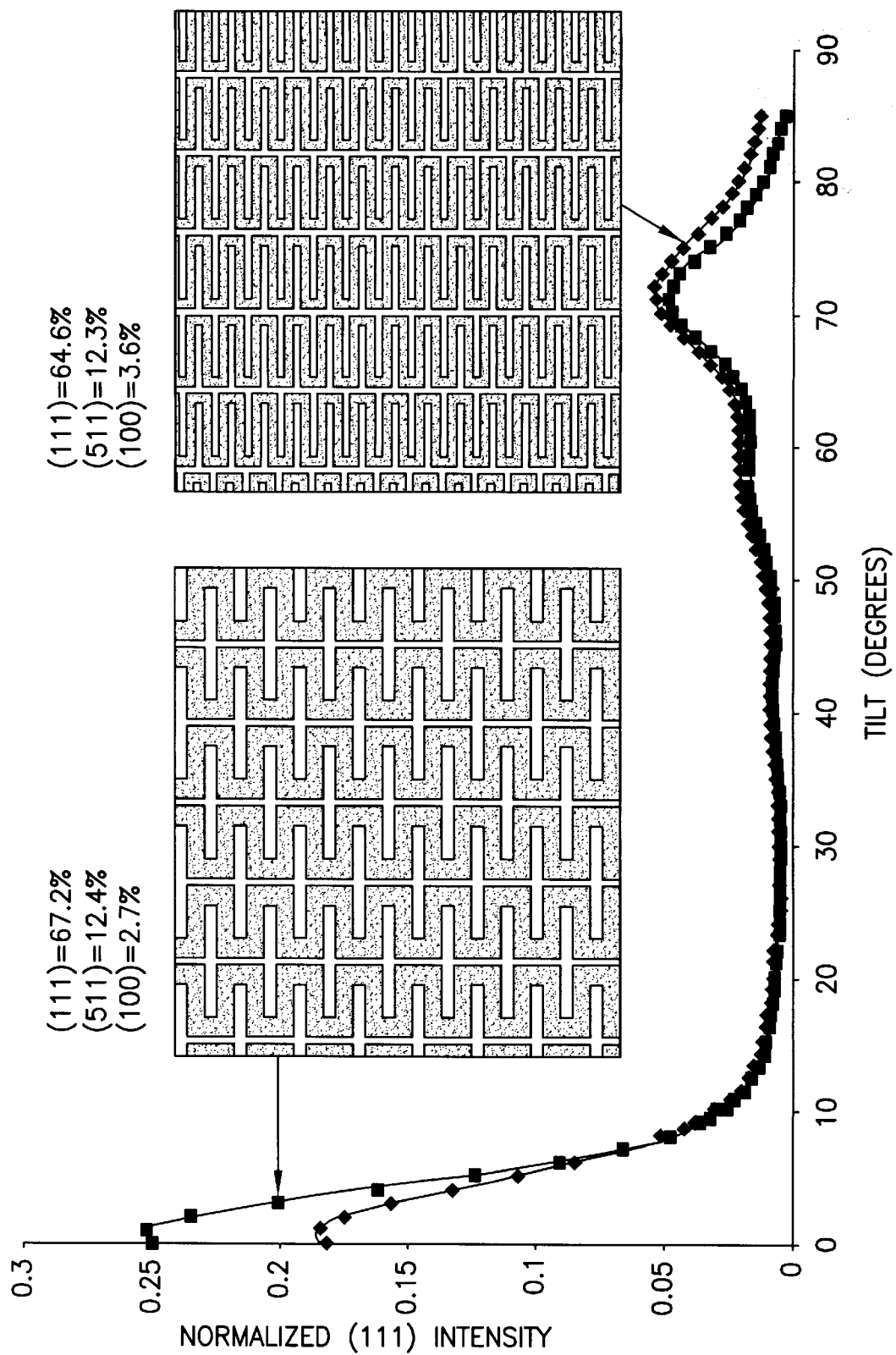
FIG. 14 shows line plots and volumetric fractions of texture components, and the associated copper pattern structures.

From the ODF the arbitrary normalized pole figures and line plots can be calculated. Additionally, the volumetric fractions of texture components are computed. The volume fraction of an orientation can be calculated by following equation:

$$V = \frac{1}{8\pi^2} * \int P(\varphi_1, \Phi, \varphi_2) * \sin(\Phi) d\varphi_1 d\Phi d\varphi_2$$

where $\Phi_1$, $\phi$ and $\Phi_2$ are the Euler angles in Bunge notation (H. J. Bunge, Texture Analysis in Materials Science (Butterworths, London, 1982). The total volume is calculated with the above equation when the range of the three Euler angles corresponding to a particular texture component is specified. An example of such analysis for copper patterned structure is shown in FIGS. 13 and 14.

The invention can be applied to the case of an even larger wafer than the given example, such as a 300 millimeter diameter wafer. The minimal fixed distance between the detector and measurement spot will be forced to a larger distance, thus the total angular range of $\chi$, $2\theta$, and $\phi$ captured within each detector frame will be smaller. This will lead to larger errors in reproducing the ODF, but the methodology applied will be the same. The motion control of very large wafers can be carried out using the same combination of motion stages (in slightly larger sizes which are readily available from commercial suppliers) with very little added cost.

In some instances of commercial quality control the full ODF might not be required. Small angular ranges of crystallographic texture variation with respect to particular directions (for example parallel or perpendicular to an interconnect line) will provide critical information with minimal data collection times. The present invention will apply to such measurements as well.

Although the invention has been variously disclosed herein with reference to illustrative embodiments and features, it will be appreciated that the embodiments and features described hereinabove are not intended to limit the invention, and that other variations, modifications and alternative embodiments will suggest themselves to those of ordinary skill in the art. The invention therefore is to be broadly construed, as including such variations, modifications and alternative embodiments within the spirit and scope of the ensuing claims.

What is claimed is:

1. A texture mapping system for determination of crystallographic texture characteristics of a generally planar sample defining an associated sample plane, said system comprising:
   a collimated source of radiation energy directing radiation energy to a measurement point on the sample;
   a 2-dimensional area detector that registers energy diffracted from the sample at the measurement point, said collimated source of radiation energy and said 2-dimensional area detector being in a fixed spatial relationship to one another and sufficiently proximate to the sample measuring point to capture a plurality of diffraction arcs within a single data capture frame of said detector;
   a sample motion assembly translating the sample in the sample plane; and
   a texture analysis processor constructed and arranged to generate texture data from the diffraction characteristics of the detected diffracted energy.

2. The texture mapping system of claim 1, wherein the radiation energy source emits monochromatic x-radiation.

3. The texture mapping system of claim 1, wherein the monochromatic x-radiation has a wavelength in the range of from about 0.5 Angstroms to about 3 Angstroms.

4. The texture mapping system of claim 1, wherein the relative positions of the collimated source of radiation energy, the 2-dimensional area detector, and the sample motion assembly, and the extent of the range of motion of the rotational motion stage, are cooperatively selectable so as to allow texture analysis by the system of wafers of at least 200 mm diameter.

5. The texture mapping system of claim 1, wherein the relative positions of the collimated source of radiation energy, the 2-dimensional area detector, and the sample motion assembly, and the extent of the range of motion of the rotational motion stage, are cooperatively selectable so as to allow texture analysis by the system of wafers up to 300 mm in diameter.

6. The texture mapping system of claim 1, wherein the sample motion assembly comprises three mutually orthogonal rectilinear translational motion stages operatively coupled together, and operatively coupled to a rotational motion stage positioned above the translational motion stages, so that any point on an uppermost surface of the sample when the sample is on the rotational motion stage may be positioned at said measurement point with any rotational orientation within the range from 0 to 360 degrees relative to a reference rotation orientation.

7. The texture mapping system of claim 6, wherein the extent of the range of motion of the rotational motion stage is restricted to the range of from 0 to 180 degrees or less.

8. The texture mapping system of claim 1, wherein resolution of texture data by the texture analysis processor from the diffracted energy data captured by the 2-dimensional area detector is determinable to 1 degree or better of resolution in the $2\Theta$ and $\chi$ directions.

9. The texture mapping system of claim 1, wherein resolution of texture data by the texture analysis processor from the diffracted energy data captured by the 2-dimensional area detector is determinable to at least 0.5 degree of resolution in the $2\Theta$ and $\chi$ directions.

10. The texture mapping system of claim 1, wherein the sample motion assembly is constructed and arranged to permit only in plane motions of the sample.

11. A texture mapping system for determination of crystallographic texture characteristics of a generally planar sample defining an associated sample plane, said system comprising:
    a collimated source of radiation energy directing radiation energy to a measurement point on the sample;
    a 2-dimensional area detector that registers energy diffracted from the sample at the measurement point, said collimated source of radiation energy and said 2-dimensional area detector being in a fixed spatial relationship to one another and sufficiently proximate to the sample measuring point to capture a plurality of diffraction arcs within a single data capture frame of said detector;
    a sample motion assembly translating the sample in the sample plane; and a texture analysis processor constructed and arranged to generate texture data from the diffraction characteristics of the detected diffracted energy, by performing a texture analysis protocol for determining ODF from severely truncated pole figures for the sample.

12. A texture mapping system for determination of crystallographic texture characteristics of a generally planar sample defining an associated sample plane, said system comprising:
    a collimated source of radiation energy directing radiation energy to a measurement point on the sample;
    a 2-dimensional area detector that registers energy diffracted from the sample at the measurement point, said collimated source of radiation energy and said 2-dimensional area detector being in a fixed spatial relationship to one another and sufficiently proximate to the sample measuring point to capture a plurality of diffraction arcs within a single data capture frame of said detector;
    a sample motion assembly translating the sample in the sample plane; and
    a texture analysis processor constructed and arranged to generate texture data from the diffraction characteristics of the detected diffracted energy, comprising computational means for:
    estimating an Orientation Distribution Function from experimental pole figures,
    calculating pole figures from the Orientation Distribution Function,
    comparing the calculated and experimental pole figures,
    estimating the error,
    modifying the Orientation Distribution Function and repeating the process beginning with calculation of the pole figures from the new Orientation Distribution Function, and
    terminating when the estimated error is within acceptable limits.

13. The texture mapping system of claim 1, which does not include any Eulerian cradle providing $\chi$ rotation, or any $\theta$–$2\theta$ goniometer component, or any similar apparatus for providing $\chi$ or $\theta$–$2\theta$ rotation.

14. A texture mapping system for determination of crystallographic texture characteristics of a generally planar sample defining an associated sample plane said system comprising:
    a collimated source of radiation energy directing radiation energy to a measurement point on the sample;
    a 2-dimensional area detector that registers energy diffracted from the sample at the measurement point, said collimated source of radiation energy and said 2-dimensional area detector being in a fixed spatial relationship to one another and sufficiently proximate to the sample measuring point to capture a plurality of diffraction arcs within a single data capture frame of said detector;

a sample motion assembly translating the sample in the sample plane; and a texture analysis processor constructed and arranged to generate texture data from the diffraction characteristics of the detected diffracted energy, wherein said texture analysis processor performs a texture analysis protocol enabling a fixed spatial relationship between the detector and the source to be determined, and the fixed angles employed to be optimized.

15. A method of determining crystallographic texture characteristics of a generally planar polycrystalline sample defining an associated sample plane, said method comprising:

irradiating a measurement point on the sample from a radiation source;

detecting energy diffracted from the sample in sufficient proximity to the sample measuring point to capture a plurality of diffraction arcs within a single data capture frame, at a detection locus in fixed spatial relationship to the radiation source;

moving the sample only in the sample plane during data aquisition; and generating texture data from the diffraction characteristics of the detected diffracted energy.

16. The method of claim 15, wherein the radiation source emits monochromatic x-radiation.

17. The method of claim 16, wherein the monochromatic x-radiation has a wavelength in the range of from about 0.5 Angstroms to about 3 Angstroms.

18. The method of claim 15, wherein the relative positions of the radiation source, the locus of detection, the sample, and the extent of the range of motion of the sample, are cooperatively selectable so as to allow texture analysis by the system of wafers of at least 200 mm diameter.

19. The method of claim 15, wherein the relative positions of the radiation source, the locus of detection, the sample, and the extent of the range of motion of the sample, are cooperatively selectable so as to allow texture analysis by the system of wafers up to 300 mm in diameter.

20. The method of claim 15, wherein the sample is moved only in the sample plane during data acquisition, by a sample motion assembly comprises three mutually orthogonal rectilinear translational motion stages operatively coupled together, and operatively coupled to a rotational motion stage positioned above the translational motion stages, so that any point on an uppermost surface of the sample when the sample is on the rotational motion stage may be positioned at said measurement point with any rotational orientation within the range from 0 to 360 degrees relative to a reference rotation orientation.

21. The method of claim 20, wherein the extent of the range of motion of the rotational motion stage is restricted to the range of from 0 to 180 degrees or less.

22. The method of claim 15, wherein resolution of texture data from the diffracted energy is determinable to 1 degree or better of resolution in the 2Θ and χ directions.

23. The method of claim 15, wherein resolution of texture data from the diffracted energy is determinable to at least 0.5 degree of resolution in the 2Θ and χ directions.

24. The method of claim 15, wherein the sample is constrained to move only in the sample plane.

25. A method of determining crystallographic texture characteristics of a generally planar polycrystalline sample defining an associated sample plane, said method comprising:

irradiating a measurement point on the sample from a radiation source;

detecting energy diffracted from the sample in sufficient proximity to the sample measuring point to capture a plurality of diffraction arcs within a single data capture frame, at a detection locus in fixed spatial relationship to the radiation source;

moving the sample only in the sample plane during data acquisition; and generating texture data from the diffraction characteristics of the detected diffracted energy, by performing a texture analysis protocol for determining ODF from severely truncated pole figures for the sample.

26. A method of determining crystallographic texture characteristics of a generally planar polycrystalline sample defining an associated sample plane, said method comprising:

irradiating a measurement point on the sample from a radiation source;

detecting energy diffracted from the sample in sufficient proximity to the sample measuring point to capture a plurality of diffraction arcs within a single data capture frame, at a detection locus in fixed spatial relationship to the radiation source;

moving the sample only in the sample plane during data acquisition; and generating texture data from the diffraction characteristics of the detected diffracted energy, by performing a texture analysis protocol comprising the steps of:

estimating an Orientation Distribution Function from experimental pole figures, calculating pole figures from the Orientation Distribution Function, comparing the calculated and experimental pole figures, estimating the error, modifying the Orientation Distribution Function and repeating the process beginning with calculation of the pole figures from the new Orientation Distribution Function, and terminating when the estimated error is within acceptable limits.

27. The method of claim 15, which does not include the use of any Eulerian cradle providing χ rotation, or any θ–2θ goniometer component, or any similar apparatus for providing χ or θ–2θ rotation.

28. A method of determining crystallographic texture characteristics of a generally planar polycrystalline sample defining an associated sample plane, said method comprising:

irradiating a measurement point on the sample from a radiation source;

detecting energy diffracted from the sample in sufficient proximity to the sample measuring point to capture a plurality of diffraction arcs within a single data capture frame, at a detection locus in fixed spatial relationship to the radiation source;

moving the sample only in the sample plane during data acquisition; and generating texture data from the diffraction characteristics of the detected diffracted energy, by performing a texture analysis protocol which enables a fixed spatial relationship between the detection locus and the radiation source to be determined, and the associated fixed angles employed to be optimized.

29. The texture mapping system of claim 12, wherein the sample motion assembly comprises three mutually orthogonal rectilinear translational motion stages operatively coupled together, and operatively coupled to a rotational motion stage positioned above the translational motion stages, so that any point on an uppermost surface of the sample when the sample is on the rotational motion stage may be positioned at said measurement point with any rotational orientation within the range from 0 to 360 degrees relative to a reference rotation orientation.

30. The texture mapping system of claim 29, wherein the extent of the range of motion of the rotational motion stage is restricted to the range of from 0 to 180 degrees or less.

31. The texture mapping system of claim 12, wherein resolution of texture data by the texture analysis processor from the diffracted energy data captured by the 2-dimensional area detector is determinable to 1 degree or better of resolution in the $2\theta$ and $\chi$ directions.

32. The texture mapping system of claim 12, wherein resolution of texture data by the texture analysis processor from the diffracted energy data captured by the 2-dimensional area detector is determinable to at least 0.5 degree of resolution in the $2\theta$ and $\chi$ directions.

33. The texture mapping system of claim 12, wherein the sample motion assembly is constructed and arranged to permit only in plane motions of the sample.

34. The method of claim 26, wherein the sample is moved only in the sample plane during data acquisition, by a sample motion assembly comprises three mutually orthogonal rectilinear translational motion stages operatively coupled together, and operatively coupled to a rotational motion stage positioned above the translational motion stages, so that any point on an uppermost surface of the sample when the sample is on the rotational motion stage may be positioned at said measurement point with any rotational orientation within the range from 0 to 360 degrees relative to a reference rotation orientation.

35. The method of claim 34, wherein the extent of the range of motion of the rotational motion stage is restricted to the range of from 0 to 180 degrees or less.

36. The method of claim 26, wherein resolution of texture data from the diffracted energy is determinable to 1 degree or better of resolution in the $2\theta$ and $\chi$ directions.

37. The method of claim 26, wherein resolution of texture data from the diffracted energy is determinable to at least 0.5 degree of resolution in the $2\theta$ and $\chi$ directions.

38. The method of claim 26, wherein the sample is constrained to move only in the sample plane.

39. A system for determining crystallographic texture characteristics of a sample, comprising:
   a radiation source for impinging radiation on said sample;
   a diffracted radiation detector for detecting diffracted radiation energy from said sample; and
   a processor constructed and arranged for texture mapping said sample from diffracted radiation energy detected by said detector, by computational and comparison steps comprising a texture analysis protocol for determining ODF of said sample.

40. A process for determining crystallographic texture characteristics of a sample, comprising:
   impinging radiation on said sample;
   detecting diffracted radiation energy from said sample; and
   texture mapping said sample from diffracted radiation energy detected by said detector, by computational and comparison steps comprising a texture analysis protocol for determining ODF of said sample.

* * * * *

UNITED STATES PATENT AND TRADEMARK OFFICE
CERTIFICATE OF CORRECTION

PATENT NO. : 6,301,330 B1
DATED : October 9, 2001
INVENTOR(S) : Kurtz et al.

It is certified that error appears in the above-identified patent and that said Letters Patent is hereby corrected as shown below:

Column 10,
Line 10, "ϕ" should be -- $\chi$ --
Line 29, "60" should be -- 60 --

Column 11,
Line 11, "θ2θ" should be -- $2\theta$ --
Line 13, "in 2 to" should be -- in $2\theta$ to --

Column 12,
Line 4, "40" should be -- 40 --
Line 17, "75" should be -- 75 --
Line 37, "1800" should be -- $180°$ --
Line 46, "4" should be -- $\phi$ --
Line 49, "20/" should be -- $2\theta$ --

Column 14,
Line 2, "a-cross-sections" should be -- $\alpha$-cross-sections --
Line 3, "B-y" should be -- B-$\gamma$ --
Line 22, "($\sigma_c$=21.6°, $\phi_c$=0°, $\phi_d$=21.6°, $\phi_d$=0°)" should be -- ($\sigma_c$=21.6°, $\phi_c$=0°, $\sigma_d$=21.6°, $\phi_d$=0°) --
Line 23, "($\sigma_c$=17.2°, $\phi^c$=0°, $\phi_d$=26.6°, $\phi_d$=35°)" should be -- ($\sigma_c$=17.2°, $\phi_c$=0°, $\sigma_d$=26.6°, $\phi_d$=35°) --
Line 60, "," should be -- $\varepsilon$ --

Column 15,
Line 58, "Appi." should be -- Appl. --

Column 18,
Line 16, "and a texture" should be -- and ¶ a texture --

Column 19,
Line 28, "and generating" should be -- and ¶ generating --

UNITED STATES PATENT AND TRADEMARK OFFICE
CERTIFICATE OF CORRECTION

PATENT NO. : 6,301,330 B1
DATED : October 9, 2001
INVENTOR(S) : Kurtz et al.

It is certified that error appears in the above-identified patent and that said Letters Patent is hereby corrected as shown below:

Column 20,
Line 51, "θ-2θ" should be -- 2θ --

Signed and Sealed this

Second Day of July, 2002

Attest:

JAMES E. ROGAN
Attesting Officer  Director of the United States Patent and Trademark Office